(12) United States Patent
Egolf et al.

(10) Patent No.: US 11,241,202 B2
(45) Date of Patent: *Feb. 8, 2022

(54) HEAD AND NECK RADIATION SHIELD STRUCTURE

(71) Applicant: Norad Designs LLC, Oviedo, FL (US)

(72) Inventors: John Barry Egolf, Oviedo, FL (US); Scott Pollak, Winter Park, FL (US)

(73) Assignee: NORAD DESIGNS LLC, Oviedo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,497

(22) Filed: Jan. 31, 2020

(65) Prior Publication Data

US 2020/0163632 A1    May 28, 2020

Related U.S. Application Data

(63) Continuation of application No. 16/434,096, filed on Jun. 6, 2019, now Pat. No. 10,555,708.

(60) Provisional application No. 62/681,991, filed on Jun. 7, 2018.

(51) Int. Cl.
*A61B 6/10* (2006.01)
*G21F 1/08* (2006.01)
*G21F 3/00* (2006.01)

(52) U.S. Cl.
CPC .............. *A61B 6/107* (2013.01); *G21F 1/085* (2013.01); *G21F 3/00* (2013.01)

(58) Field of Classification Search
CPC . A61B 6/107; G21F 1/08; G21F 1/085; G21F 1/125; G21F 3/00
See application file for complete search history.

(56) References Cited

U.S. PATENT DOCUMENTS 6,325,538 B1    12/2001  Heesch
6,481,888 B1 *  11/2002  Morgan ................. A61B 6/107
                                                    250/515.1

(Continued)

FOREIGN PATENT DOCUMENTS

CN    202342062 U    7/2012
CN    202761308 U    3/2013

(Continued)

OTHER PUBLICATIONS

Lorenzi, "Latest Advances in Health Care Cleaning and Disinfection Chemicals", Health Facilities Management, 2017). (Year: 2017).*

(Continued)

*Primary Examiner* — David E Smith
(74) *Attorney, Agent, or Firm* — Foley & Lardner LLP

(57) ABSTRACT

A shield structure configured to protect a head and/or neck of a patient during a radiologic procedure comprises a bottom wall, a side wall, and an opening. The bottom wall includes radiation attenuating material and is configured to be positioned between the head and/or neck of the patient and a radiation source so as to shield the patient from radiation directed toward the bottom of the patient. The bottom wall is of a general size to shield the head and/or neck of the patient. The side wall includes radiation attenuating material and is configured to extend upward from the bottom wall so as to shield the patient from radiation directed toward a side of the patient. The opening is configured to receive the head and/or neck of the patient.

19 Claims, 20 Drawing Sheets

(56) References Cited

U.S. PATENT DOCUMENTS

| | | | |
|---|---|---|---|
| 7,667,214 B2 * | 2/2010 | Cadwalader | A61B 6/107 250/515.1 |
| 7,829,873 B2 | 11/2010 | Fox et al. | |
| 9,271,685 B1 * | 3/2016 | Cadwalader | G21F 1/125 |
| 2008/0276554 A1 * | 11/2008 | Sheetz | G21F 1/125 52/239 |
| 2012/0049093 A1 | 3/2012 | Costea | |
| 2012/0273622 A1 * | 11/2012 | Long | G21F 1/06 244/171.7 |
| 2016/0038103 A1 * | 2/2016 | Cadwalader | A61B 6/107 250/515.1 |
| 2016/0158082 A1 | 6/2016 | Gainor et al. | |
| 2017/0119324 A1 * | 5/2017 | Wilson | A61B 6/107 |
| 2017/0332984 A1 | 11/2017 | Brendel et al. | |
| 2020/0100736 A1 * | 4/2020 | Lemer | G21F 3/00 |

FOREIGN PATENT DOCUMENTS

| | | | |
|---|---|---|---|
| CN | 203169204 U | * | 9/2013 |
| CN | 105913891 B | | 2/2018 |

OTHER PUBLICATIONS

Cano O,Alonso P., Osca J., et al., Initial experience with a new image integration module designed for reducing radiation exposure during electrophysiological ablation procedures. J Cardiovasc Electrophysial, 2015; 26: 662-670.

Huelke DF. An Overview of Anatomical Considerations of Infants and Children in the Adult World of Automobile Safety Design. Annual Proceedings / Association for the Advancement of Automotive Medicine. 1998;42:93-113.

International Search Report and Written Opinion mailed Aug. 27, 2019 in corresponding International Application No. PCT/US2019/035879, 10 pages.

Lorenzi, Latest advances in health care cleaning and disinfection chemicals, Health Facilities Management, Aug. 2, 2017 [retrieved on Aug. 1, 2019]. Retrieved from the internet; URL:https://www.hfmmagazine.com/articles/3025-cleaning-and-disinfection-chemicals-for-health-care, entire document.

National Research Council. Health Risks Health Risks from Exposure to Low Levels of Ionizing Radiation: BEIR VII Phase 2. Washington, D.C.: National Academies, 2006, ISBN:0-309-58771-9, 12 pages (http://www.nap.edu/catalog/9526.html).

Notice of Allowance on U.S. Appl. No. 16/434,096 dated Sep. 30, 2019.

Valderrabano M, Greenberg S, Razavi H, et al. 3D cardiovascular navigation system: accuracy and reduction in radiation exposure in left ventricular lead implant. J Cardiovasc Electrophysiol, 2014; 25: 87-93.

International Preliminary Examination Report and Transmittal received in International Application No. PCT/US2019/035879 dated Dec. 17, 2020, 9 pages.

* cited by examiner

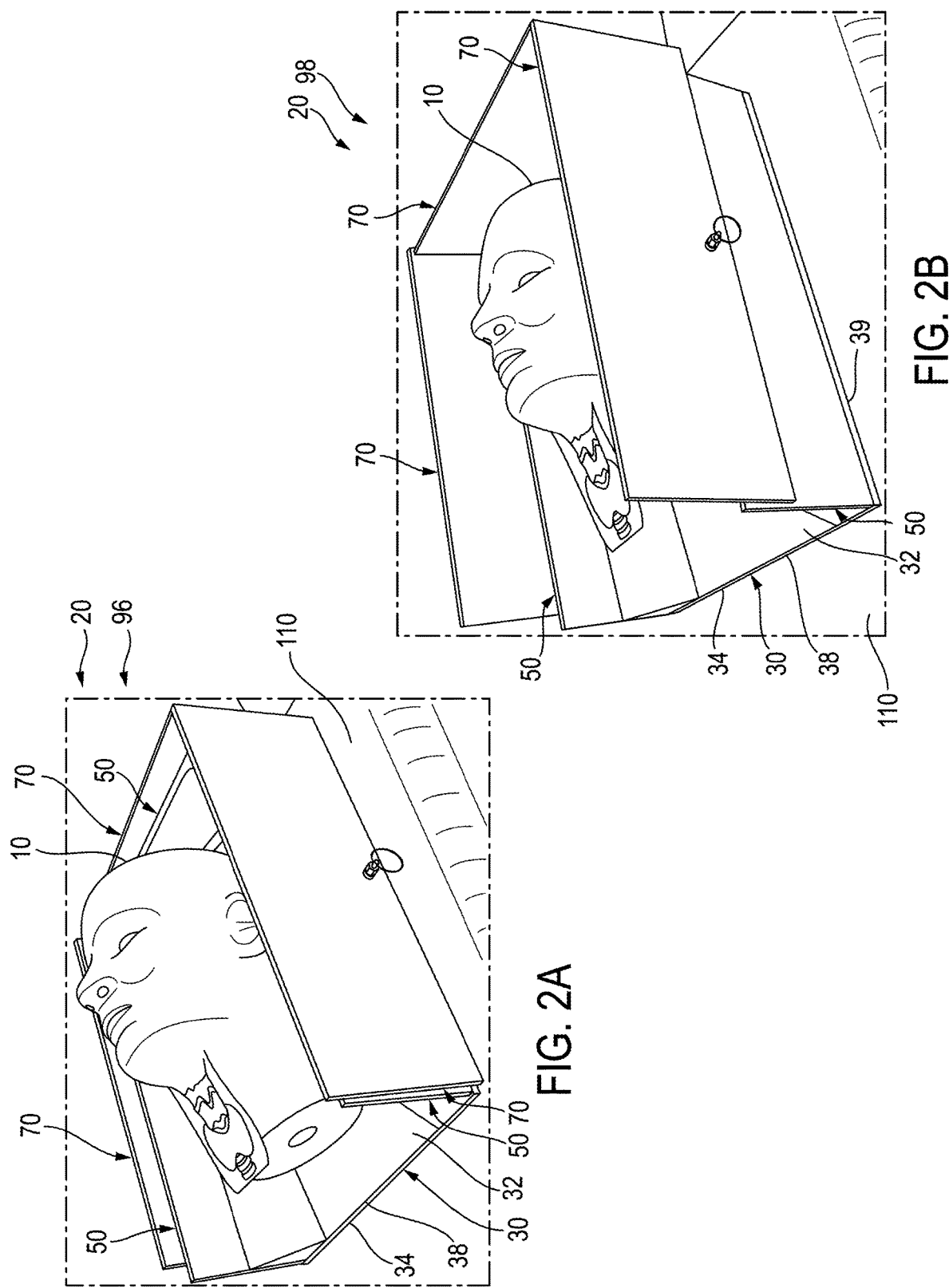

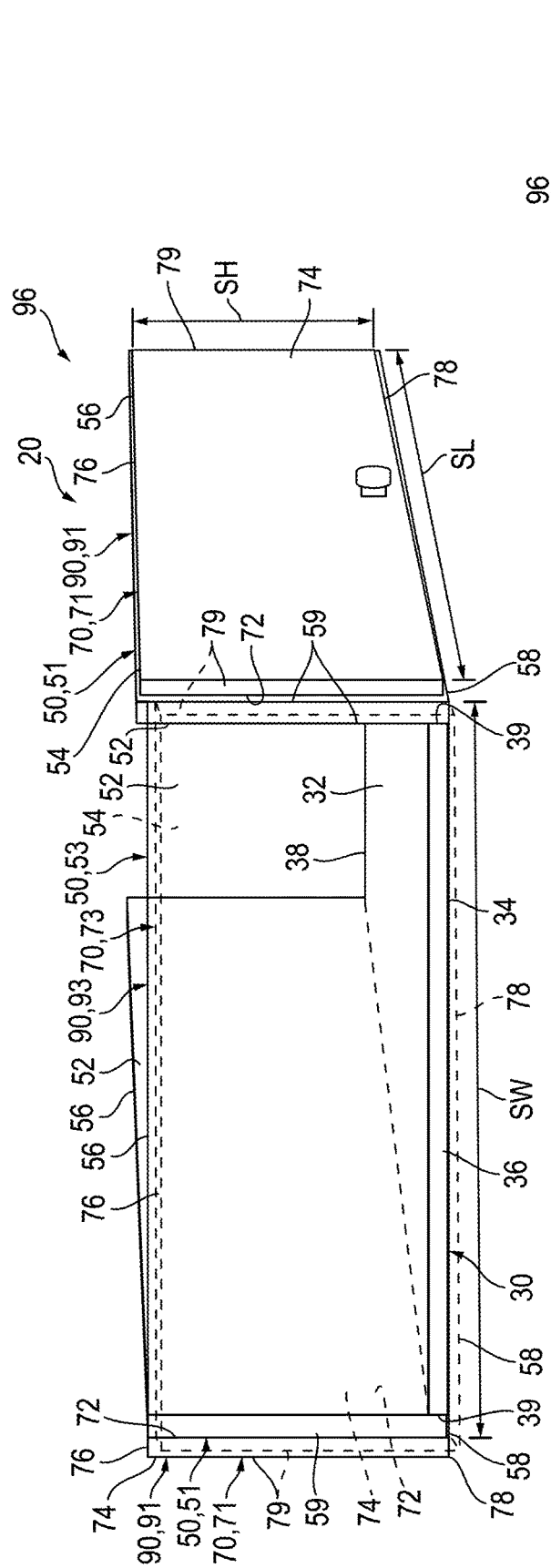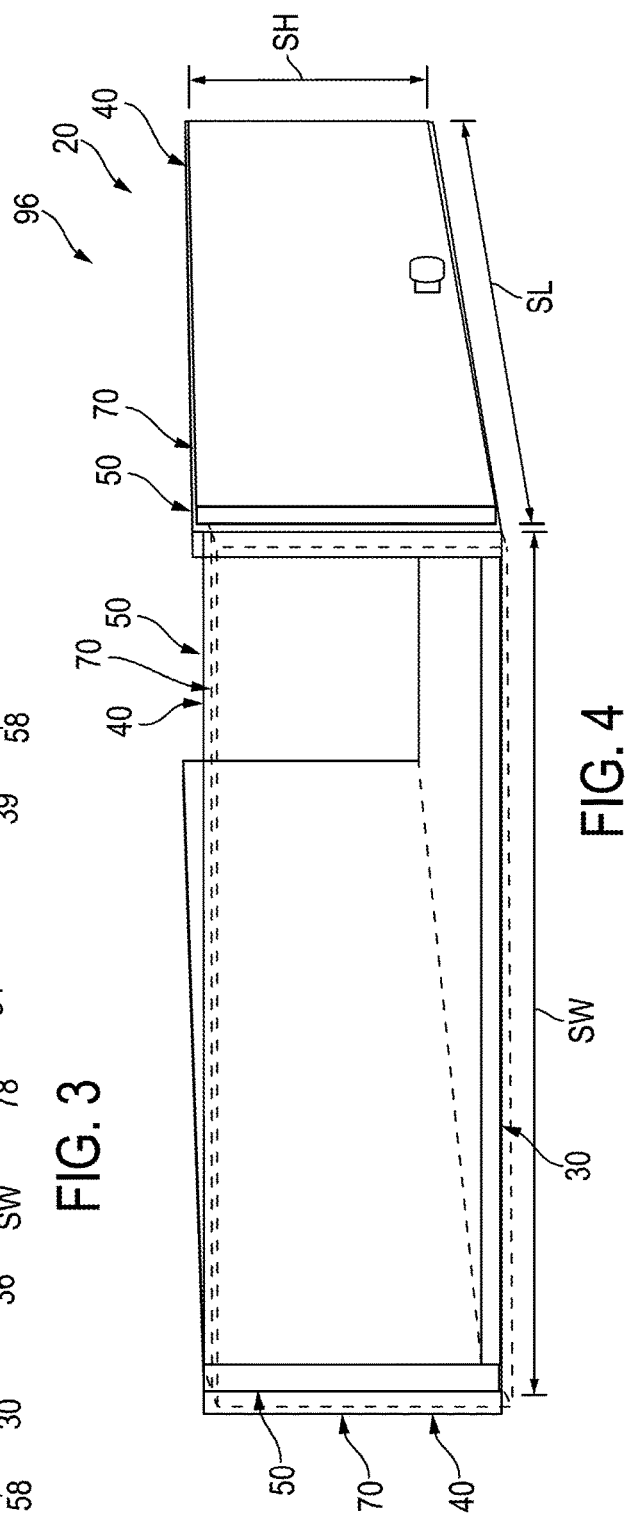

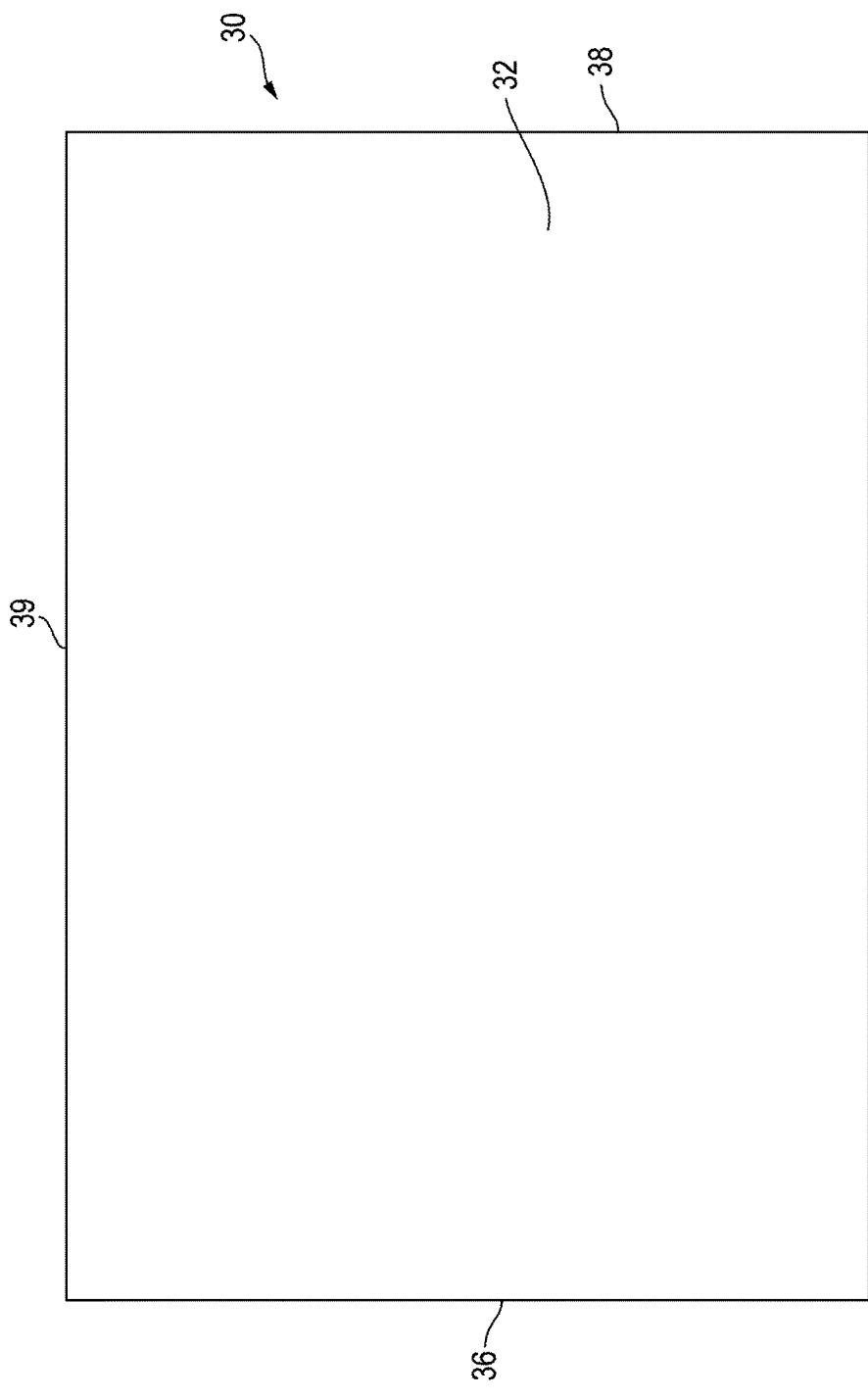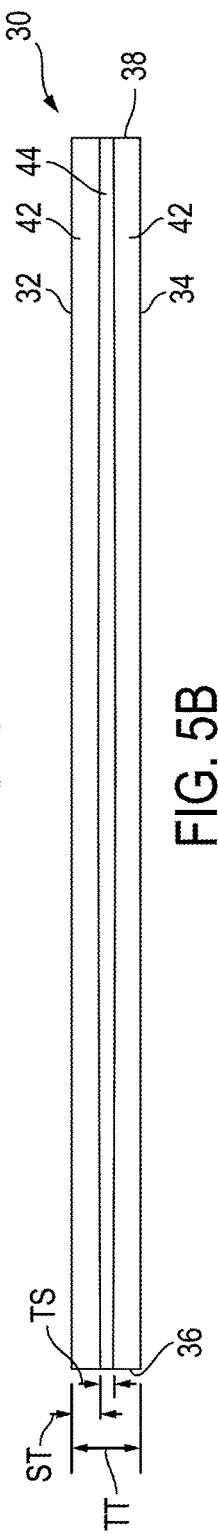

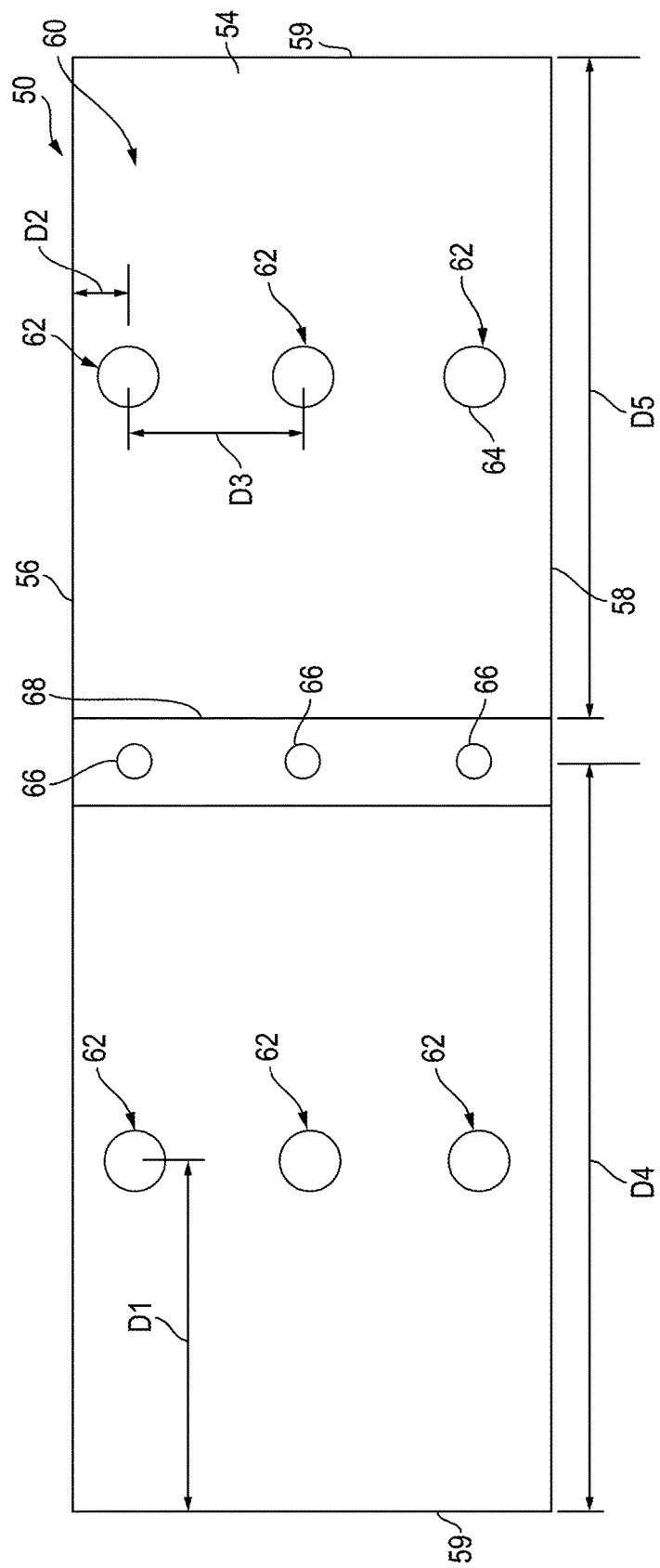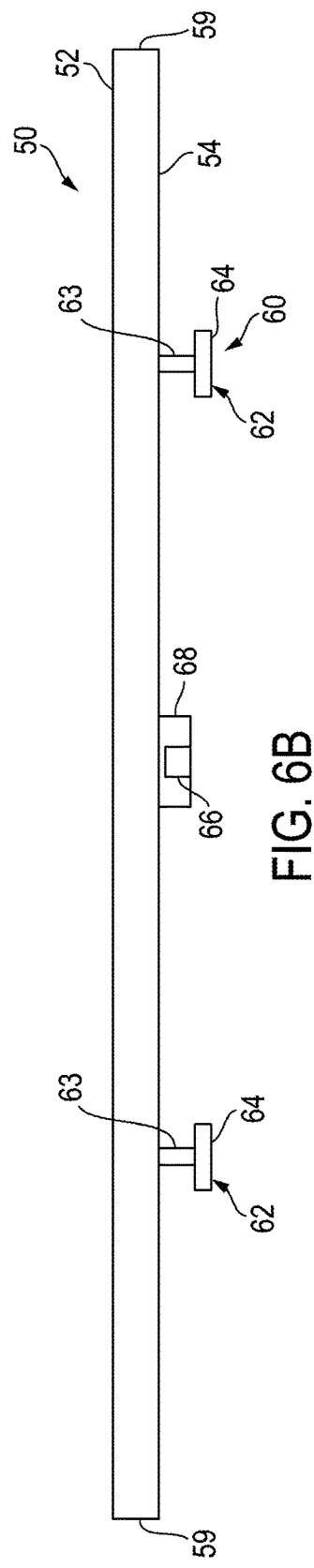
FIG. 6A
FIG. 6B

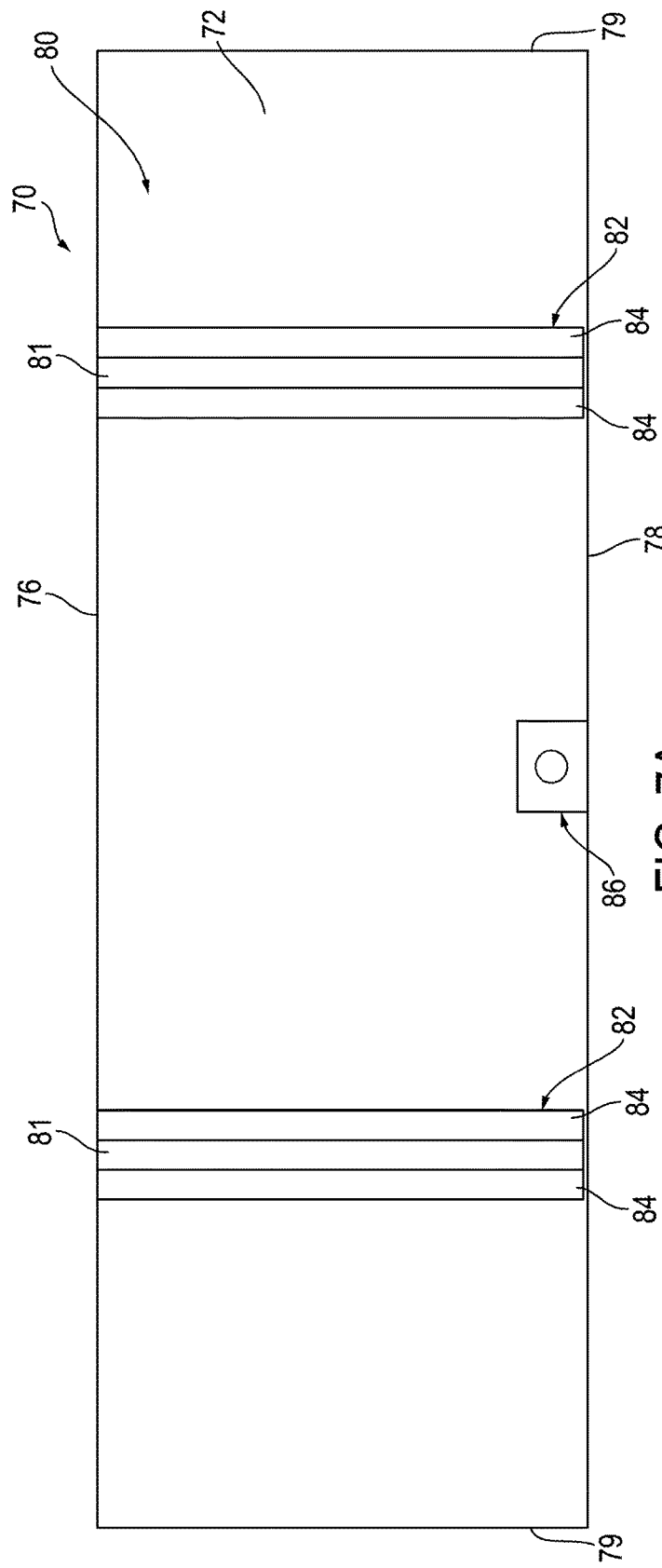
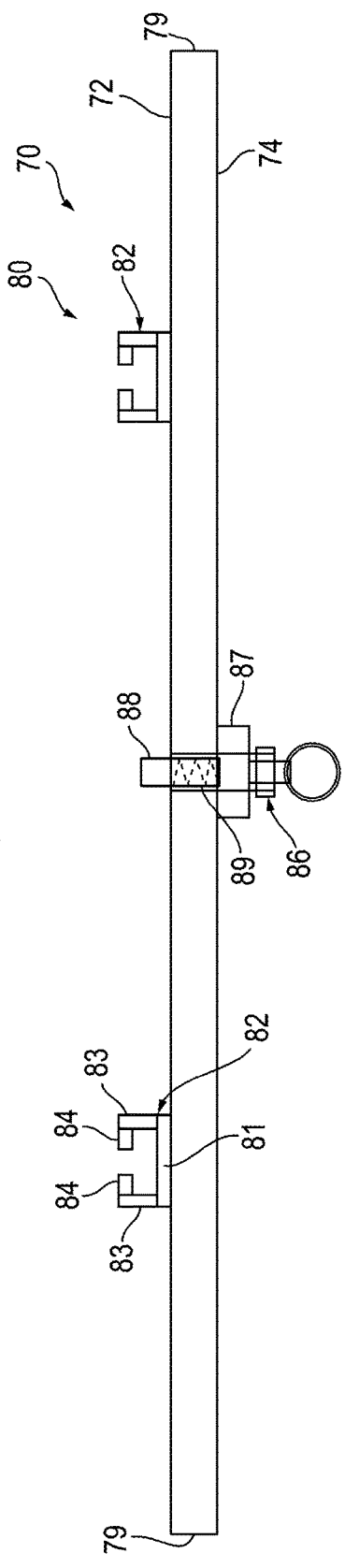
FIG. 7A
FIG. 7B

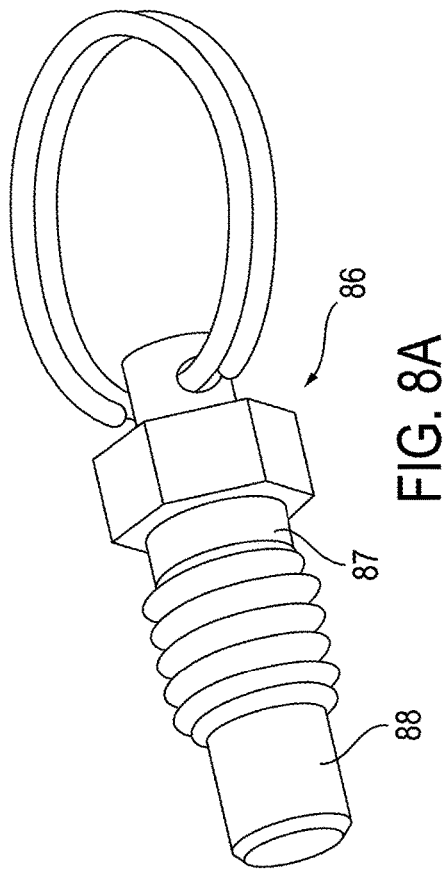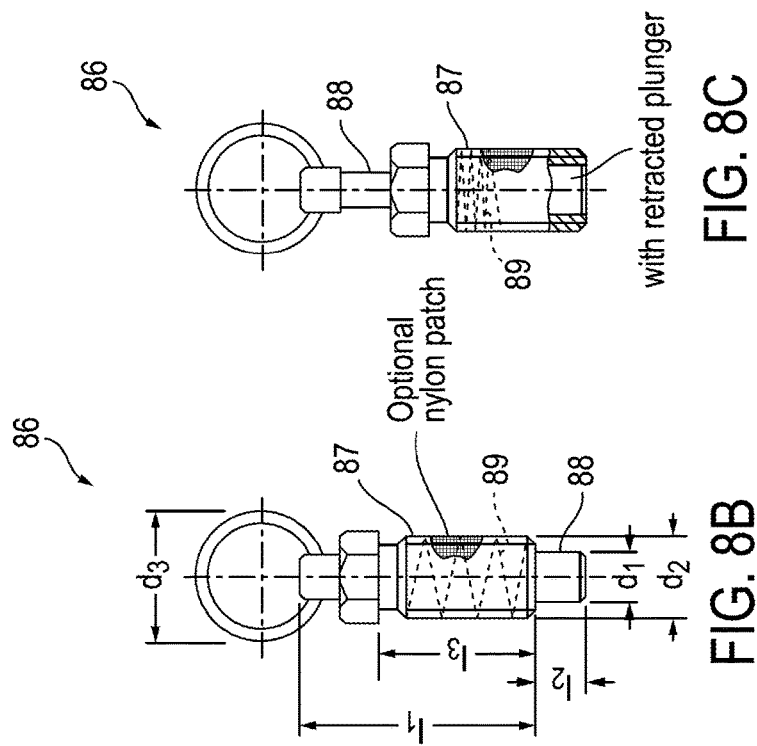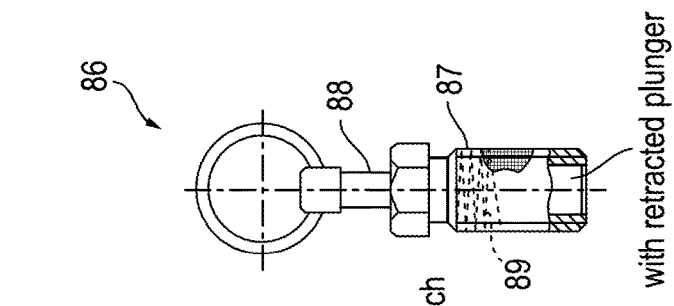

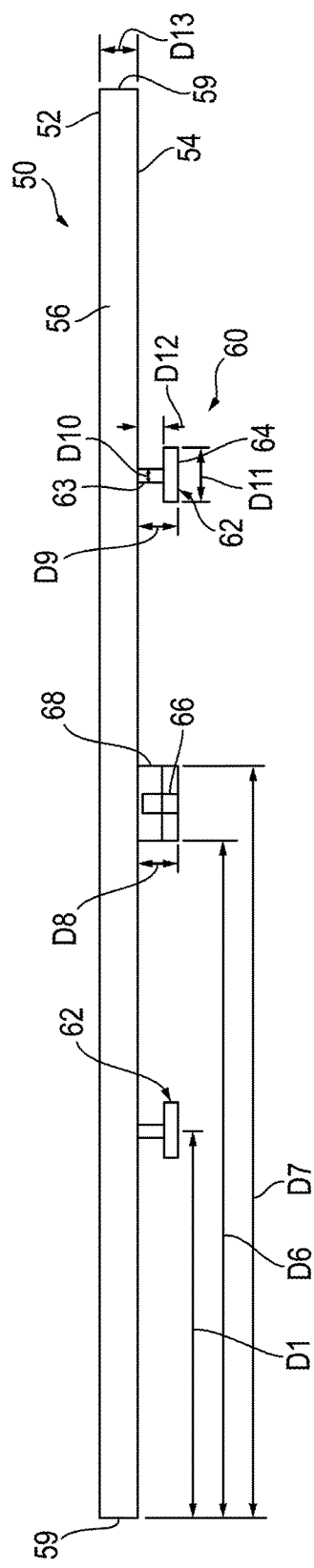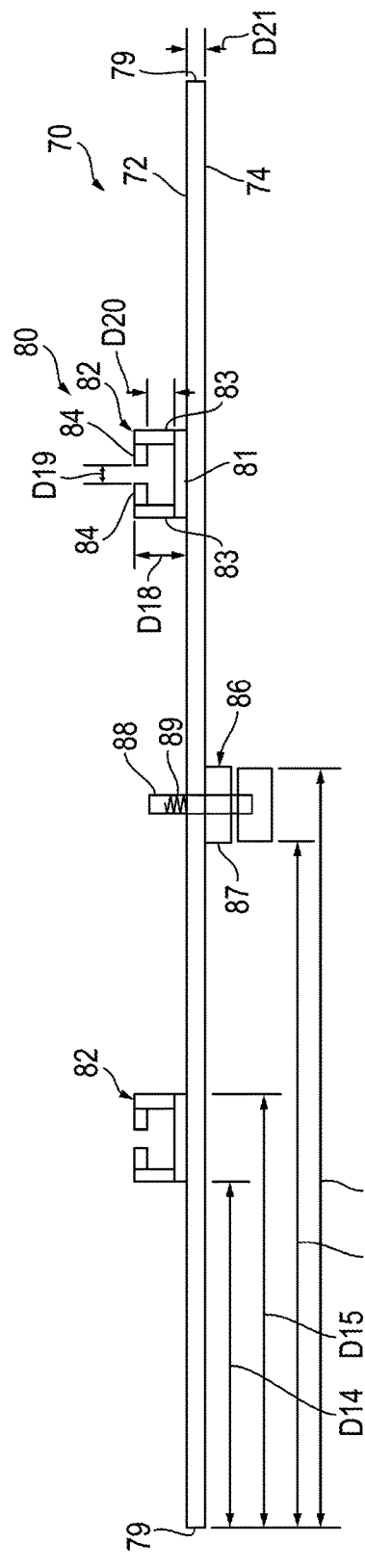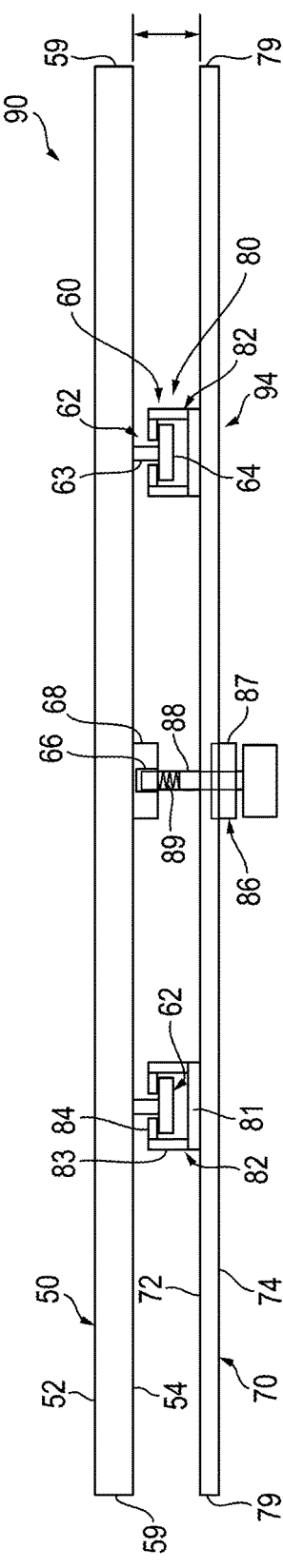

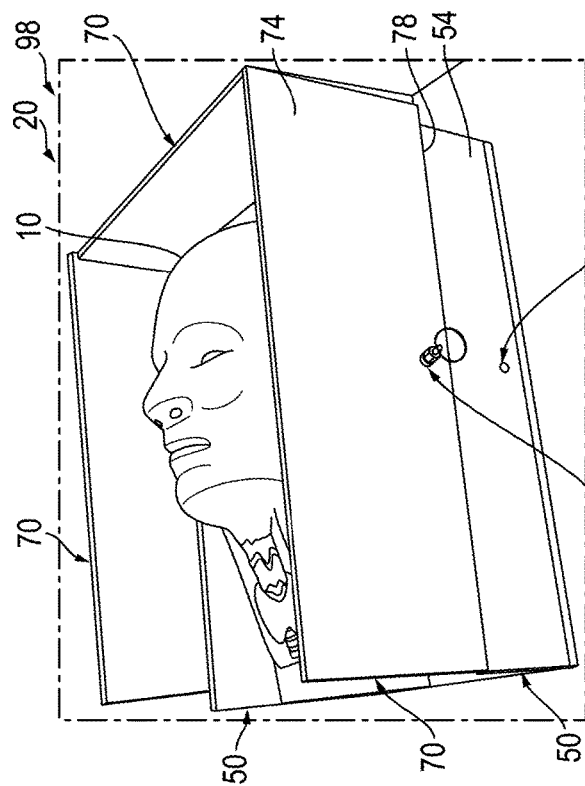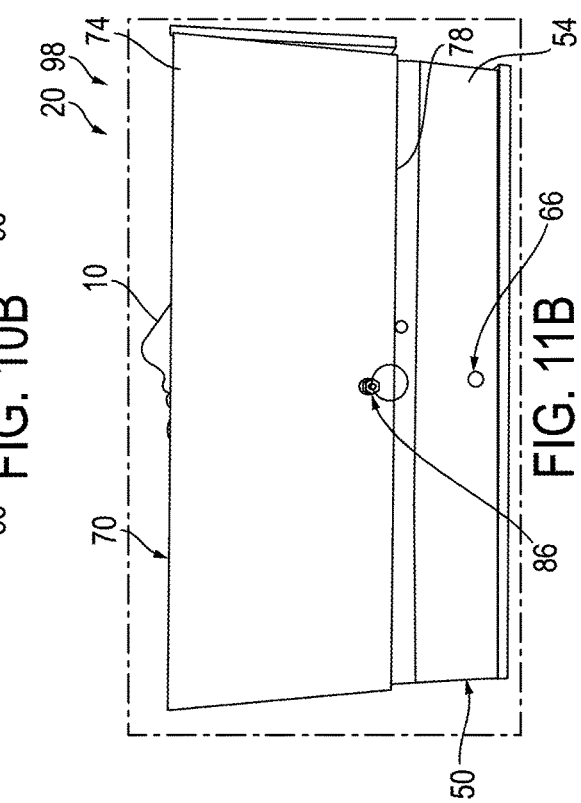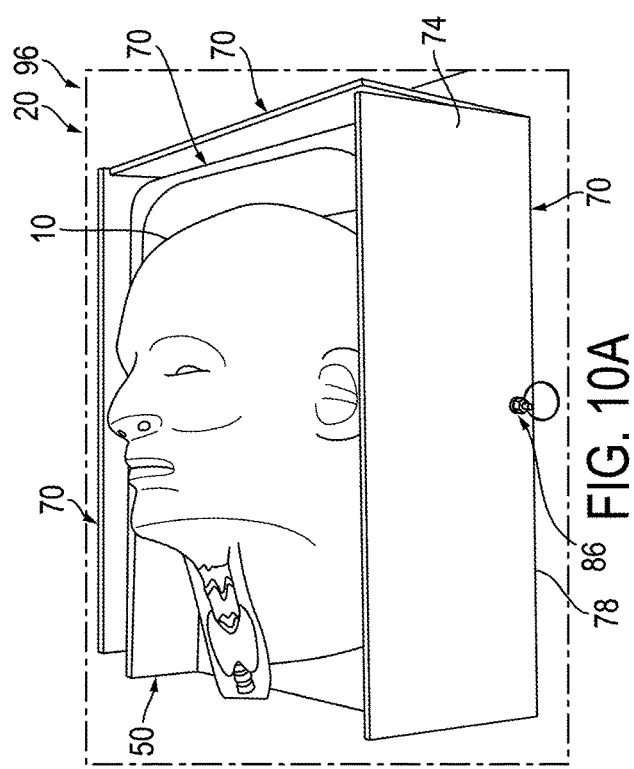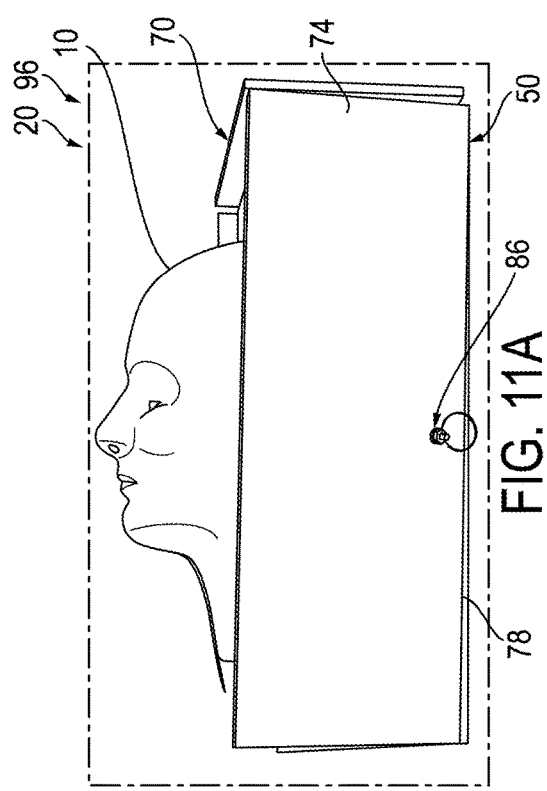

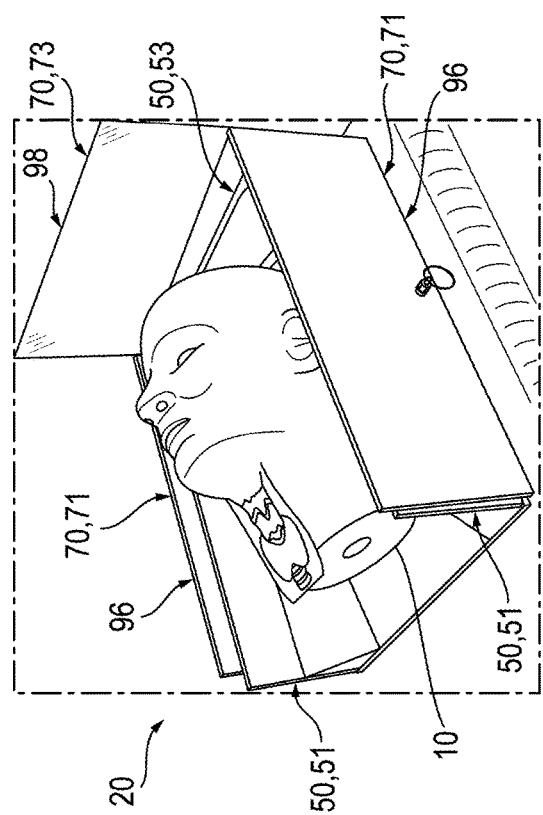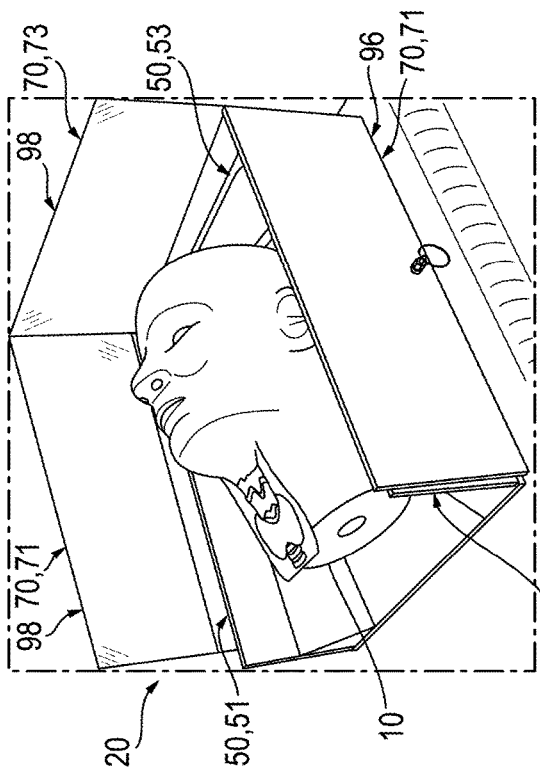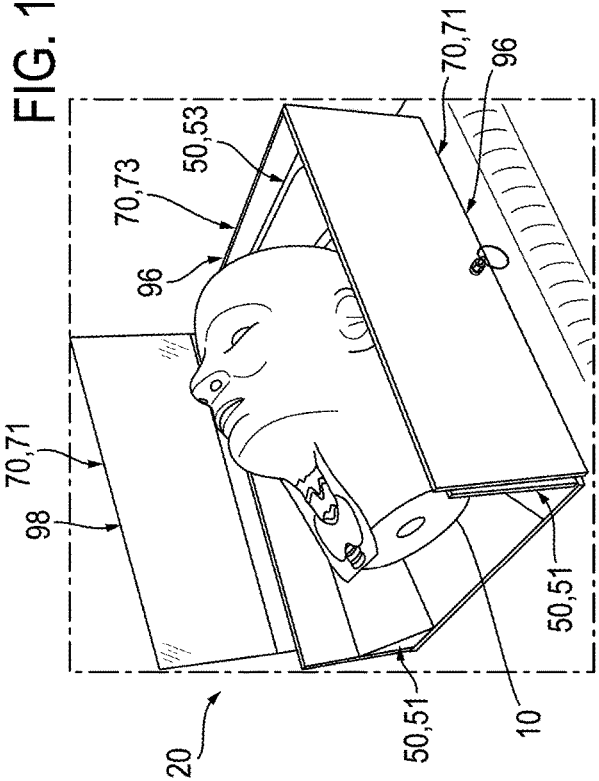

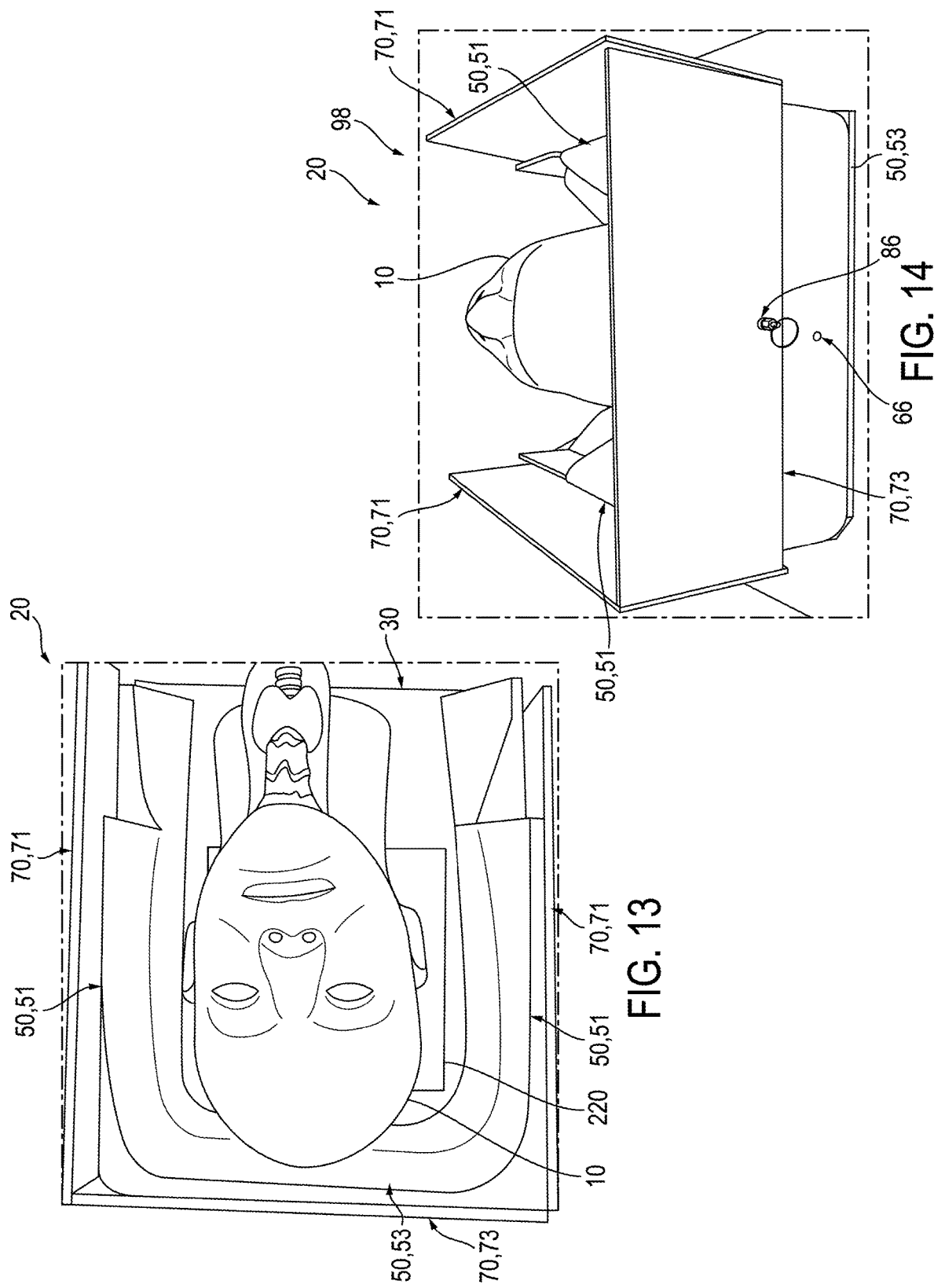

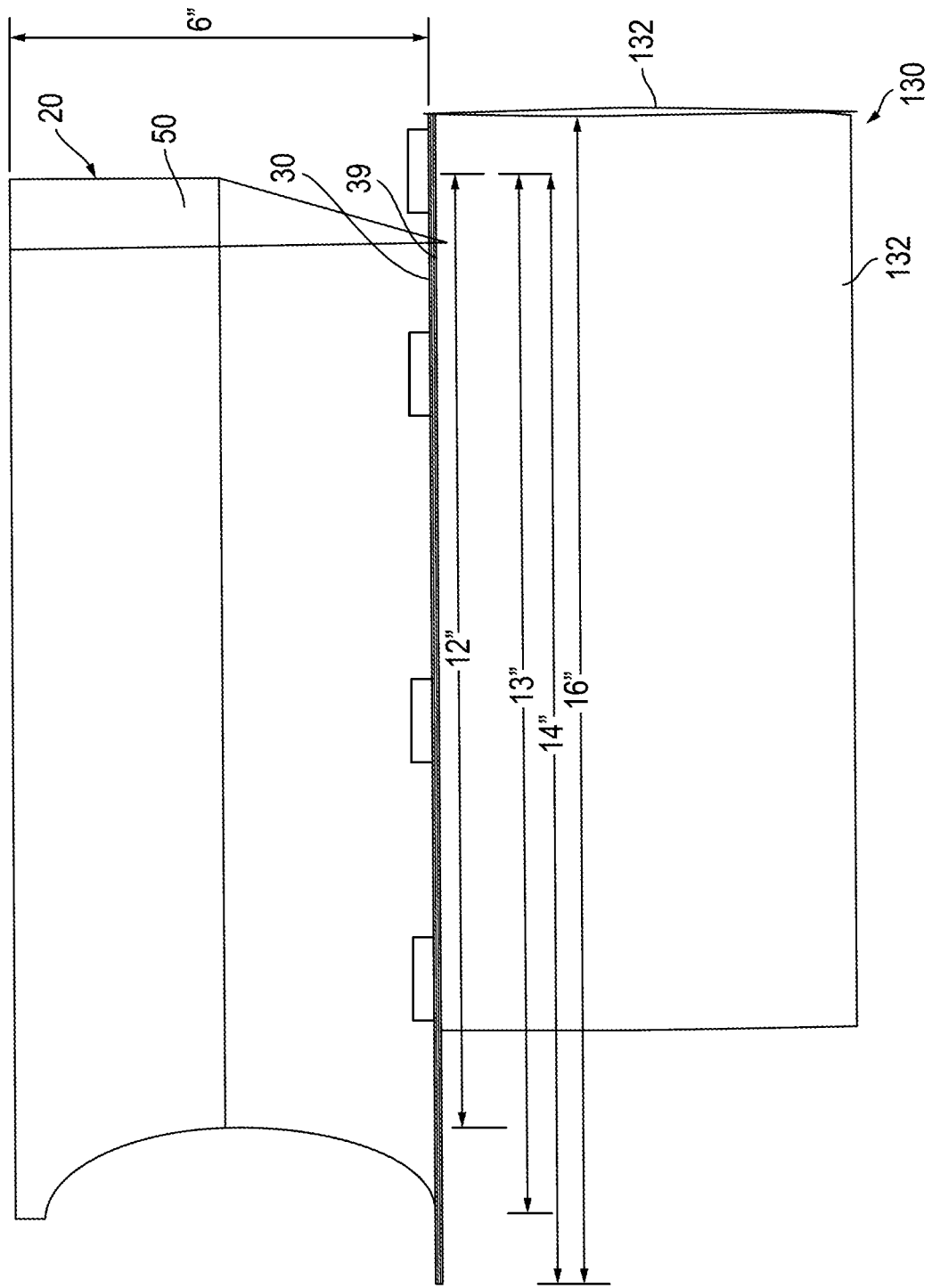

HEAD AND NECK RADIATION SHIELD STRUCTURE

CROSS REFERENCE TO RELATED APPLICATIONS

This application is a continuation of, and claims priority to co-pending U.S. patent application Ser. No. 16/434,096 filed Jun. 6, 2019 which claims the benefit of and priority to U.S. Provisional Application No. 62/681,991 filed Jun. 7, 2018, the disclosures of all of which are incorporated herein by reference in their entireties.

FIELD

This disclosure relates generally to head and neck radiation shield structures.

BACKGROUND

Radiation exposure is detrimental to human health. For example, a comprehensive review of available biologic and biophysical data supports a "no-threshold" risk model for radiation exposure since the risk of cancer may increase linearly at low doses of radiation without a threshold. Radiation has the potential to cause a small increased risk of malignancy in humans. (National Research Council. *Health Risks from Exposure to Low Levels of Ionizing Radiation: BEIR VII Phase* 2. Washington, D.C.: National Academies, 2006.) The head and neck (in particular the brain, eyes, and thyroid) are particularly sensitive to radiation. Accordingly, radiation exposure to the head and neck may be particularly detrimental to the health of the patient.

However, many different medical radiologic procedures or examinations, such as electrophysiological procedures, cardiac catheterization, angioplasty, cardiac stenting, cardiac valve procedures, and orthopedic procedures, require the use of radiation. Although many different technologies attempt to avoid or minimize radiation during these procedures, there is still a moderate to high x-ray exposure as evidenced by reported fluoroscopy in numerous studies. (Cano O, Alonso P, Osca J, et al. *Initial experience with a new image integration module designed for reducing radiation exposure during electrophysiological ablation procedures*. J Cardiovasc Electrophysial, 2015; 26: 662-670, Valderrabano M, Greenberg S, Razavi H, et al. *3D cardiovascular navigation system: accuracy and reduction in radiation exposure in left ventricular lead implant*. J Cardiovasc Electrophysiol, 2014; 25: 87-93.) Implant procedures may incur a higher exposure to the practitioner since the x-ray generator may be closer to the practitioner.

As shown in FIG. 17, during a radiologic procedure, a radiation source 120, such as an x-ray tube below a table 110 holding the patient 10, may emit radiation 122 (e.g., x-rays) as an active or direct radiation beam 121 that is aimed toward an examination area 12 of the patient's body (i.e., the area of the patient's body that is intended to be examined and is therefore intended to be exposed to radiation 122) in order to expose the examination area 12 to radiation 122 and thereby allow the examination area 12 to be examined. Most of the direct radiation beam 121 enters into the patient's body in order to expose the examination area 12 to radiation 122 and allow the examination area 12 to be examined and subsequently exits the patient's body. The examination area 12 of the patient 10 receives some radiation 122 due to the direct radiation beam 121. The entrance radiation dose 124 is the amount of radiation 122 (both from the direct radiation beam 121 and any scatter radiation 123) that enters into the patient's body, and the exit radiation dose 126 is the amount of radiation 122 that exits from the patient's body.

However, the emitted radiation 122 comprises both the direct radiation beam 121 and scatter radiation 123. In particular, some radiation 122 from the direct radiation beam 121 deflects, which causes the radiation 122 to scatter and form "scatter radiation 123." Scatter radiation 123 refers to any radiation 122 that is outside of the direct radiation beam 121. A portion of the radiation 122 may scatter before and/or after the radiation 122 enters into and exits from the patient's body. Some of the scatter radiation 123 enters into areas of the patient's body that are not under examination, such as the patient's head and neck (as shown in FIG. 17). Accordingly, these areas of the patient's body not under examination are also exposed to and receive radiation 122 due to the scatter radiation 123, which needlessly increases the patient's overall exposure to radiation 122 (i.e., the entrance radiation dose 124) and also increases the amount of radiation 122 exiting the patient 10 (i.e., the exit radiation dose 126), which may enter into and affect the practitioners.

The practitioners are also exposed to the radiation 122, including both the scatter radiation 123 that has not entered the patient's body and the scatter radiation 123 that has entered and exited the patient's body (i.e., the exit radiation dose 126). The scatter radiation 123 from areas of the patient's body that are not under examination, in particular the patient's head and neck, needlessly increases the amount of radiation 122 that the practitioners are exposed to.

In order to reduce the amount of radiation 122 that the practitioners are exposed to (specifically due to the radiation 122 exiting the patient), lead skirts that are attached to the side of the table 110, mobile shields, suspended plexiglass shields, and sterile pads placed on top of or above the patient 10 may be used. However, most of these devices are only designed to shield the practitioners from the radiation 122 exiting the patient 10. These devices do not protect the patient 10, in particular the patient's head and neck, from excessive radiation 122 (e.g., scatter radiation 123) that enters into these areas of the patient's body not under examination (in particular the patient's head and neck) and instead allow the patient to be needlessly exposed to the scatter radiation 123. Additionally, conventional shielding may not easily be moved to allow visualization of certain anatomical structures when needed.

Therefore, certain procedures, such as cardiac catheterization, expose areas of the patient's body that do not need to be visualized (such as the patient's head and neck, which includes their thyroid) to radiation 122, which needlessly increases both the patient's and the practitioner's overall exposure to radiation 122.

In order to support and stabilize the patient's head (and neck) during radiologic procedures, a conventional non-shielding head support 220 (as shown in FIGS. 18A-21C) may be placed on the table 110 and underneath the patient's head. These non-shielding supports 220 provide a relatively comfortable surface for the patient 10 to rest their head on and prevent the patient's head from moving during the radiologic procedure. The non-shielding supports 220 do not provide any shielding from radiation 122 to the patient 10 or reduce any radiation exposure in order to prevent interference with the radiologic procedure.

The non-shielding supports 220 may have a variety of different configurations as shown in FIGS. 18A-21C. For example, as shown in FIGS. 18A-18B, the non-shielding support 220 may be a gel pad that is shaped like a horseshoe. The non-shielding support 220 of FIGS. 18A-18B is specifically made out of a dry, viscoelastic polymer that is x-ray translucent, radiolucent, and non-conductive. As shown, the non-shielding support 220 of FIGS. 18A-18B includes a keyhole cutout in the middle, which provides a clear air passageway for the patient and aids the anesthesiologist while the patient's body and head are in a variety of different positions. For example, the patient 10 may be laying in a prone, lateral, or side-facing position, and the patient's head may be straight or turned to the side while using the non-shielding support 220, depending on the procedure. The non-shielding support 220 can be sized in order to be suitable for adults or pediatric/neonatal patients. As shown in FIG. 19, the non-shielding support 220 may be a contoured, foam pad or pillow. As shown in FIG. 20, the non-shielding support 220 may be a plastic brace. As shown in FIGS. 21A-21C, the non-shielding support 220 may be a contoured, carbon fiber support.

SUMMARY

Various embodiments provide for a shield structure configured to protect a head and/or neck of a patient during a radiologic procedure that comprises a bottom wall, a side wall, and an opening. The bottom wall includes radiation attenuating material and is configured to be positioned between the head and/or neck of the patient and a radiation source so as to shield the patient from radiation directed toward the bottom of the patient. The bottom wall is of a general size to shield the head and/or neck of the patient. The side wall includes radiation attenuating material and is configured to extend upward from the bottom wall so as to shield the patient from radiation directed toward a side of the patient. The opening is configured to receive the head and/or neck of the patient.

Various other embodiments provide for a method of protecting a head and/or neck of a patient during a radiologic procedure. The method comprises positioning the head and/or neck of the patient in a shield structure and exposing the patient to radiation to conduct the radiologic procedure. The shield structure has a bottom wall that includes radiation attenuating material and is positioned between the head and/or neck of the patient and a radiation source and a side wall that includes radiation attenuating material and extends upward from the bottom wall.

These and other features (including, but not limited to, retaining features and/or viewing features), together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIG. 2A is a perspective view of the shield structure of FIG. 1A in the retracted position.

FIG. 2B is a perspective view of the shield structure of FIG. 1A in the extended position.

FIG. 3 is a perspective view of the shield structure of FIG. 1A with certain dimensions according to one embodiment.

FIG. 4 is a perspective view of the shield structure of FIG. 1A with certain dimensions according to another embodiment.

FIG. 5A is a top view of a lower wall of the shield structure of FIG. 1A.

FIG. 5B is a cross-sectional view of the lower wall of FIG. 5A.

FIG. 6A is a side view of a static wall of the shield structure of FIG. 1A.

FIG. 6B is a cross-sectional view of the static wall of FIG. 6A.

FIG. 7A is a side view of a movable wall of the shield structure of FIG. 1A.

FIG. 7B is a cross-sectional view of the movable wall of FIG. 7A.

FIG. 8A is a perspective view of a fastener according to one embodiment.

FIG. 8B is a side view of the fastener of FIG. 8A in an extended position.

FIG. 8C is a side view of the fastener of FIG. 8A in a retracted position.

FIG. 8D is a top view of the fastener of FIG. 8A.

FIG. 9A is a cross-sectional view of a static wall according to one embodiment.

FIG. 9B is a cross-sectional view of a movable wall according to one embodiment.

FIG. 9C is a cross-sectional view of the static wall of FIG. 9A and the movable wall of FIG. 9B attached to each other.

FIG. 10A is a perspective view of the shield structure of FIG. 1A in the retracted position.

FIG. 10B is a perspective view of the shield structure of FIG. 1A in the extended position.

FIG. 11A is a side view of the shield structure of FIG. 1A in the retracted position.

FIG. 11B is a side view of the shield structure of FIG. 1A in the extended position.

FIG. 12A is a perspective view of the shield structure of FIG. 1A with only the top movable wall in the extended position.

FIG. 12B is a perspective view of the shield structure of FIG. 1A with only one of the side movable walls in the extended position.

FIG. 12C is a perspective view of the shield structure of FIG. 1A with only the top movable wall and one of the side movable walls in the extended position.

FIG. 13 is a top view of the shield structure of FIG. 1A.

FIG. 14 is a rear view of the shield structure of FIG. 1A in the extended position.

FIG. 26 is a side view of the shield structure of FIG. 24 without skirts.

DETAILED DESCRIPTION

Referring generally to the figures, disclosed herein is a head and neck radiation shield structure, as shown according to exemplary embodiments, that may be used to protect the head and neck of a patient from harmful ionizing radiation by minimizing, reducing, blocking, decreasing, or stopping at least portions of radiation from entering into the head and neck (in particular the thyroid) of the patient during radiology procedures. The head and neck radiation shield structure reduces penetration of radiation into the patient's head and neck (which includes the thyroid) during radiologic procedures in which the patient's head and neck are not directly involved in the imaging field and are not intended to be examined, while still allowing the practitioner to easily access the patient's head and neck. Accordingly, the head and neck radiation shield structure protects both the patient and the practitioners by reducing or minimizing both the patient's and the practitioners' overall exposure to ionizing radiation during radiology procedures or examinations.

The head and neck radiation shield structure still allows other areas of the patient's body (that are outside of the patient's head and neck region) to be exposed to ionizing radiation in order to allow these areas to be examined through radiation. Due to the potential health consequences of radiation exposure to a patient's head and neck, it is highly beneficial to use the head and neck radiation shield structure to reduce or block radiation exposure to the patient's head and neck.

Head and Neck Radiation Shield Structure

Figure 1A:
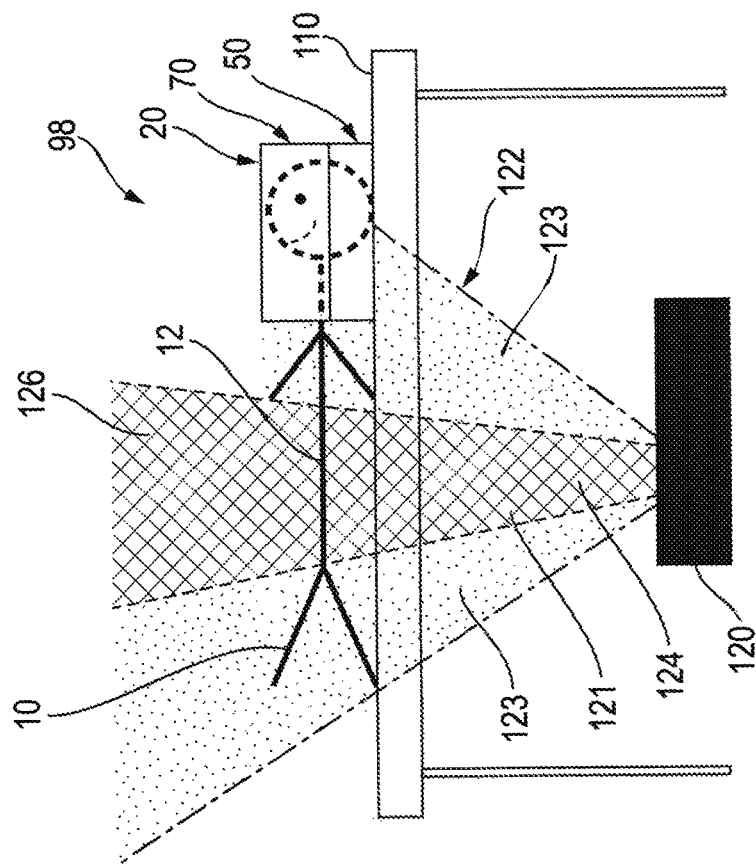
FIG. 1A is a side view of a head and neck radiation shield structure on an examination table and in a retracted position according to one embodiment.
Figure 1B:
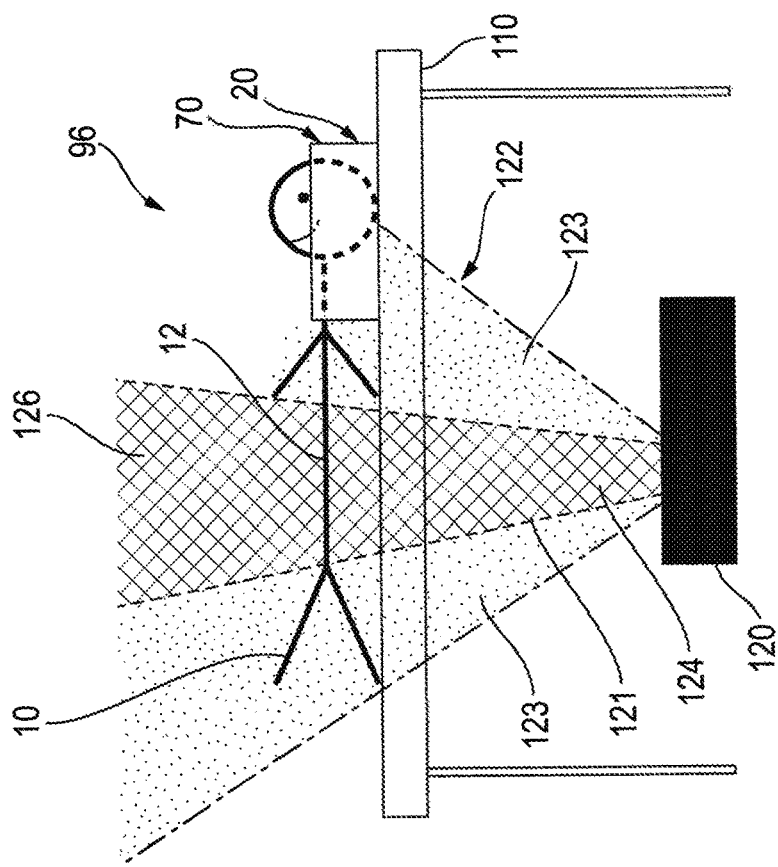
FIG. 1B is a side view of the shield structure of FIG. 1A in an extended position.

As shown in FIGS. 1A-1B, the patient 10 may lay on the procedure, radiology, or examination table 110 during a radiology procedure. The table 110 may, for example, be a horizontal table constructed out of a material that does not materially affect emitted radiation (e.g., clear plexiglass or carbon fiber). The radiation source 120 may be positioned underneath the table 110 and emit radiation 122 (e.g., x-rays) from underneath the table 110. Accordingly, the radiation 122 moves through the table 110 and toward an examination area 12 of the patient's body. The head and neck radiation shield structure 20 is configured to be used within radiologic procedures in which at least a portion of the head and neck regions of the patient's body are not intended to be examined (and therefore do not need to be exposed to ionizing radiation).

Figure 17:
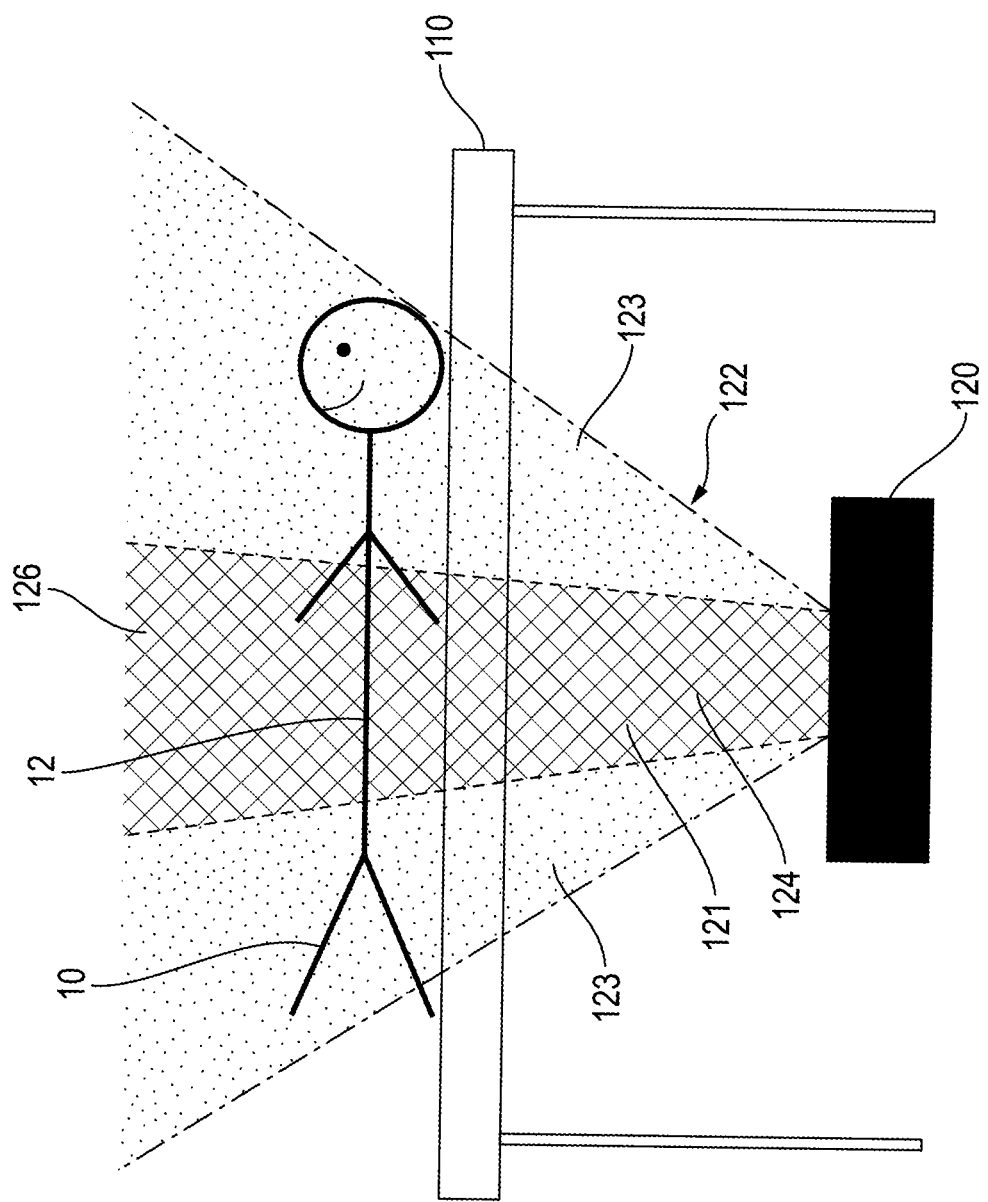
FIG. 17 is a side view of a patient on a radiation table during a radiologic procedure.
Figure 18:
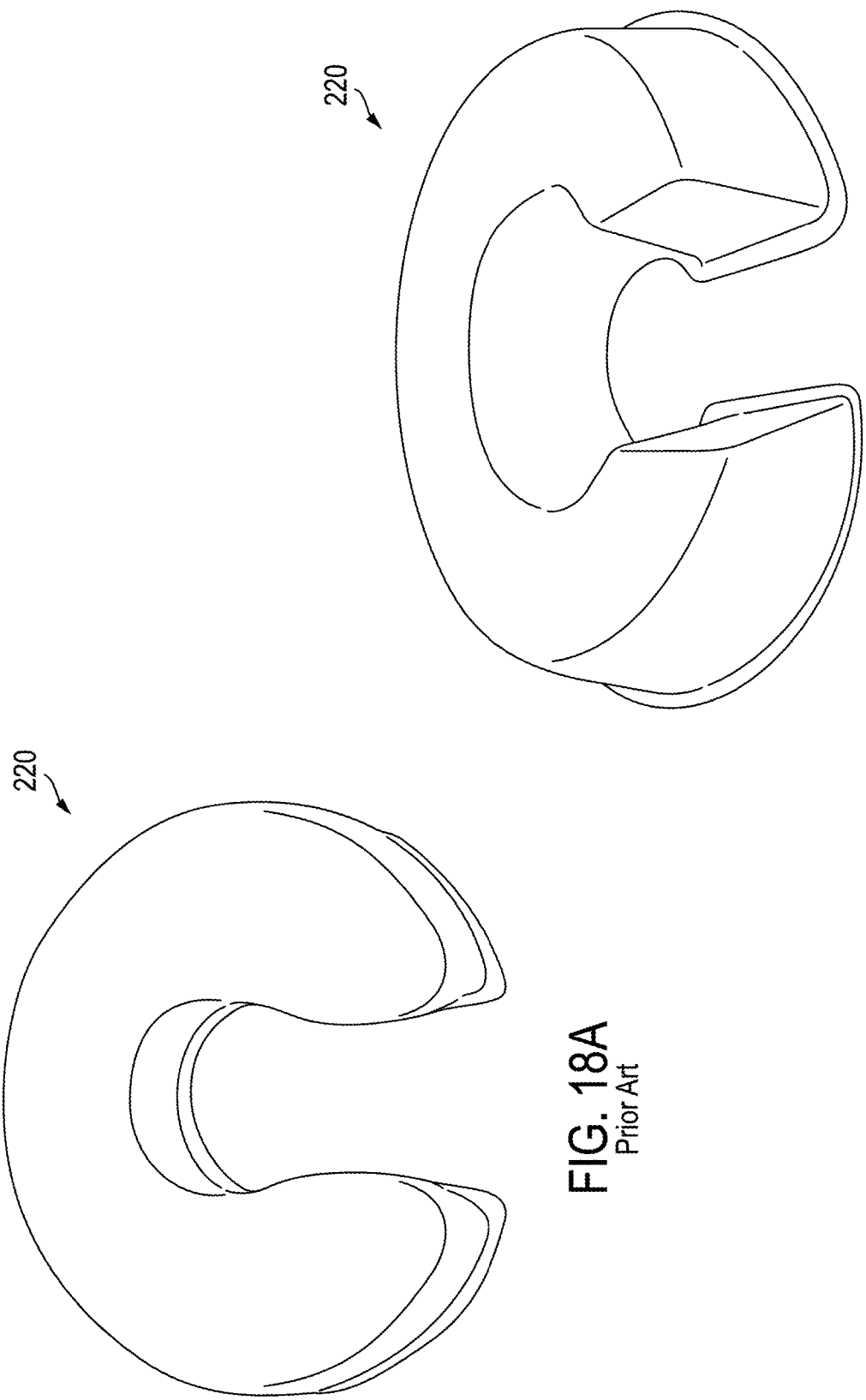
FIGS. 18A-18B are perspective views of conventional non-shielding head supports.
Figure 19:
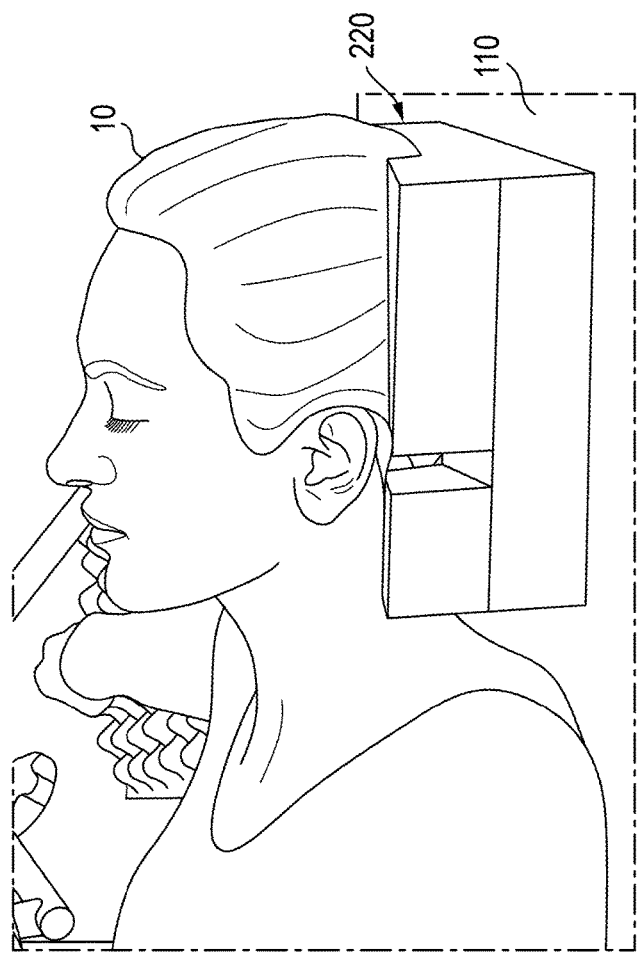
FIG. 19 is a side view of a conventional non-shielding head support.
Figure 20:
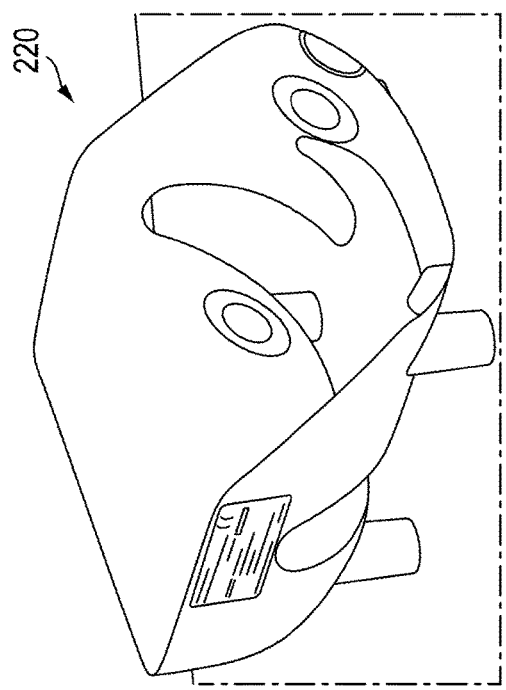
FIG. 20 is a perspective view of a conventional non-shielding head support.
Figures 21A, 21B, 21C:
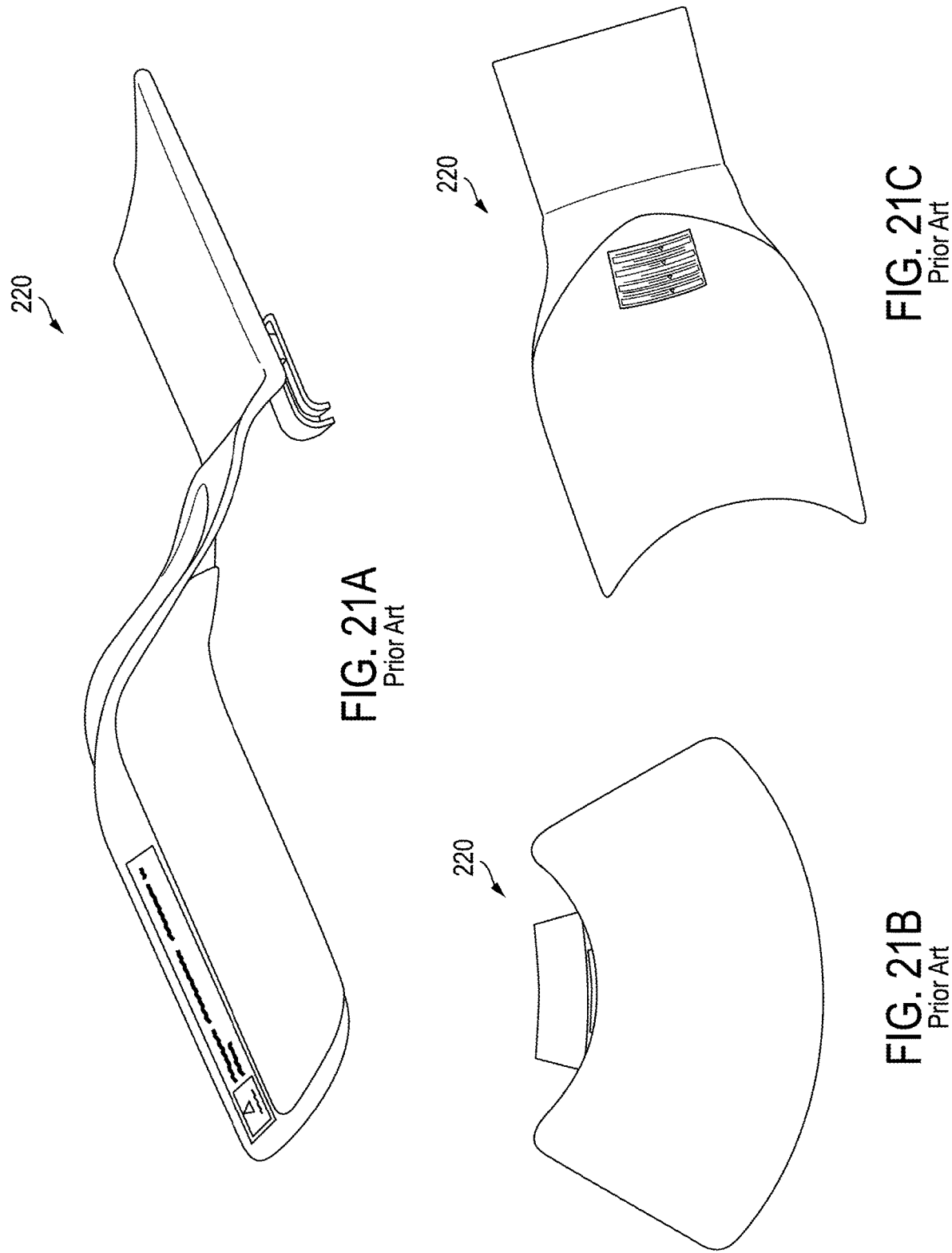
FIG. 21A is a side view of a conventional non-shielding head support.
FIG. 21B is a front view of the conventional non-shielding head support of FIG. 21A.
FIG. 21C is a top view of the conventional non-shielding head support of FIG. 21A.

As shown in FIG. 17 and described further herein, some of the radiation 122 during a radiologic procedure is deflected outside of the direct radiation beam 121 and instead is emitted as scatter radiation 123. Without the head and neck radiation shield structure 20, the scatter radiation 123 (and/or the direct radiation beam 121) may be directed to and enter into a variety of different areas of the patient's body outside of the examination area 12, including the head and neck region of the patient 10.

As shown in FIGS. 1A-1B, the head and neck radiation shield assembly or structure (referred to herein as the "shield structure 20") protects the head and neck region of the patient 10 (which includes the patient's thyroid) from being exposed to radiation 122 during radiologic procedures. Accordingly, the shield structure 20 protects both the patient and the practitioners (e.g., the doctors, physicians, medical staff, and operators) that are nearby the patient 10 from excessive and unnecessary exposure to radiation by selectively blocking or preventing radiation 122 (in particular, the scatter radiation 123) from unnecessarily entering into the patient's head and neck region. The shield structure 20 still, however, allows the examination area 12 of the patient 10 to be exposed to radiation 122 for examination purposes.

Accordingly, the shield structure 20 significantly reduces the overall amount of radiation exposure to (i.e., the amount of radiation 122 traveling through) both the patient 10 and the practitioners by preventing radiation 122 from entering into the patient's head and neck region, which reduces the amount of entrance radiation dose 124 to the patient 10. By reducing the amount of entrance radiation dose 124 into the patient 10, the amount of exit radiation dose 126 from the patient 10 is reduced, which thus reduces the practitioners' exposure to radiation. The shield structure 20 shields the patient 10 from radiation 122 in four critical areas: the left anterior oblique area, the right anterior oblique area, the cranial area, and the posterior area.

The shield structure 20 is a shell or structure that blocks radiation from entering into the patient's head and neck. According to one embodiment as shown in FIGS. 2A-4 and described further herein, the shield structure 20 comprises a wall structure that comprises at least one wall that shields various sides of the patient's head and neck. In particular, the wall structure shields the back (or front, depending on the position of the patient), sides, and/or top of the patient's head and neck. The wall structure may extend around one side or multiple sides of the patient's head and neck. For example, the wall structure may be configured to be positioned between the patient's head and neck and the top surface of the table 110. Alternatively or additionally, the wall structure may extend vertically above the table 110 such that the shield structure 20 extends vertically along at least a portion of the patient's head and neck.

According to one embodiment, as described further herein, the wall structure of the shield structure 20 comprises a plurality of walls (e.g., a lower or bottom wall 30 and at least one static or side wall 50). The static wall 50 may be a part of a wall set 90 that optionally further includes a movable side wall 70. According to one embodiment, the shield structure 20 may be a box with four enclosed sides (i.e., the lower wall 30 and three static or side walls 50 (e.g., a front wall, a first side wall portion, and a second side wall portion) and two open sides. The two open sides provide an area for the patient's neck to extend along and allow the practitioner to easily access the patient during the radiologic procedure.

As described further herein, the movable walls 70 are each independently movable between a retracted position 96 and an extended position 98 relative to the static walls 50 and the lower wall 30 in order to provide either more shielding or more access to the patient's head and neck along different areas of the patient's head and neck, according to the desired configuration and the specific procedure. However, the shield structure 20 still provides shielding and protection to the patient's head and neck, regardless of the position of the movable walls 70.

According to another embodiment, the wall structure of the shield structure 20 comprises only one single wall that may be created as one continuous, unitary wall that is constructed as an integral, single-piece and cannot be separated without destruction. The single wall of the wall structure may be flat or curved and may extend around one or multiple sides of the patient's head and neck during use. According to one embodiment, the single wall may substantially extend only horizontally along the top surface of the table 110 in a substantially horizontal orientation such that, during use, the single wall extends along only the back of the patient's head and neck (when the patient is lying with their back on the table 110). According to another embodiment, the single wall may substantially extend only vertically above the top surface of the table 110 in a substantially vertical orientation such that, during use, the single wall extends along only a side or top of the patient's head and neck (when the patient is lying with their back on the table 110). According to another embodiment, the single wall may curve around at least a portion of the patient's head and neck (i.e., along 2, 3, or 4 sides of the patient's head and neck) in a substantially "U" shape. For example, the single wall may comprise a first portion that is the lower wall 30 and a second portion that is the static wall 50, where the lower wall 30 and the static wall 50 are created as one continuous, curved wall that is constructed as an integral, single-piece and cannot be separated without destruction.

Figure 15:
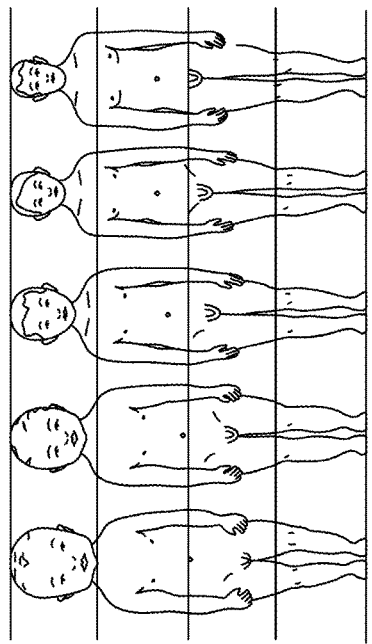
FIG. 15 is a depiction of the proportion of different body segments compared to age, as illustrated by Huelke D F.
Figure 16:
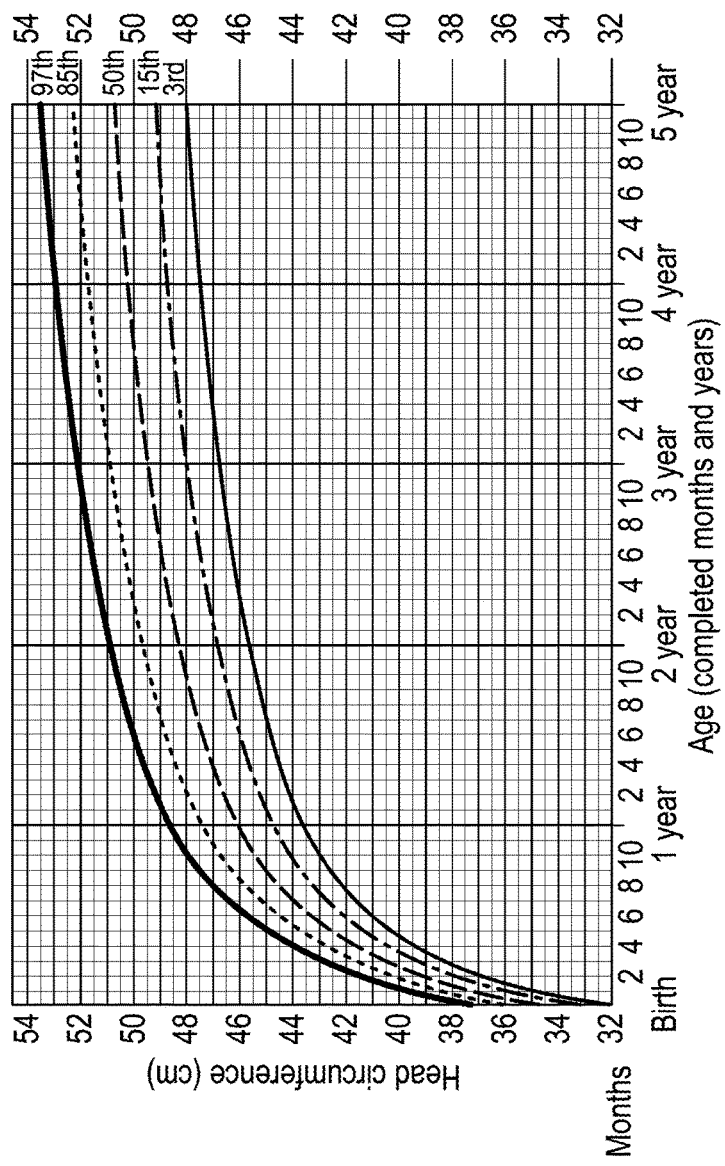
FIG. 16 is a graph of head circumference of boys compared to their age, as documented by the World Health Organization.

As shown in FIGS. 3-4, the shield structure 20 may have a variety of different dimensions, according to the desired configuration and use. For example, the shield structure 20 may be shaped, sized, and proportioned in order to be optimally suitable for an adult patient (as shown with the shield structure 20 in FIG. 3) or to be optimally suitable for a pediatric patient, such as a neonatal patient, an infant, a baby, or a child (as shown with the shield structure 20 in FIG. 4). (Additionally, the shield structure 20 may also be shaped, sized, and proportioned in order to be optimally suitable for adolescents.) By having different sizes and proportions for adult patients compared to pediatric patients, the shield structure 20 can most effectively shield the patient 10 according to their head and neck size and proportion. The proportion of various body segments, in particular the head compared to the rest of the body, in adults compared to pediatrics is substantially different, as shown in FIG. 15. (Huelke D F. An Overview of Anatomical Considerations of Infants and Children in the Adult World of Automobile Safety Design. *Annual Proceedings/Association for the Advancement of Automotive Medicine.* 1998; 42:93-113, which states that "at birth the head is one-fourth the total body length, whereas the adult it is one-seventh.") Additionally, the World Health Organization documents that the head circumference of pediatrics under the age of one year increases substantially more rapidly than the head circumference of pediatrics between the ages of one and five years, as shown in FIG. 16.

In order to account for the proportional differences between adult patients and pediatric patients, the shield structure 20 may be sized and proportioned accordingly. In particular, the shield structure 20 for pediatric patients may have a relatively more square shape (i.e., may be proportionally more wide) than the shield structure 20 for adult patients in order to more adequately accommodate for the head of the pediatric patient (which may be proportionally more wide than the head of an adult patient). For example only, for an adult patient (as shown with the shield structure 20 in FIG. 3), the shield structure height SH (while in the retracted position 96) may be approximately 5 inches, the shield structure length SL may be approximately 15 inches, and the shield structure width SW may be approximately 12 inches. For a pediatric patient (as shown with the shield structure 20 in FIG. 4), the shield structure height SH (while in the retracted position 96) may be approximately 3 inches, the shield structure length SL may be approximately 10 inches, and the shield structure width SW may be approximately 10 inches.

For reference, the shield structure length SL extends along the side edges 39 of the lower wall 30, and the shield structure width SW extends along the top edge 36 of the lower wall 30 (where the bottom edge 38 of the lower wall 30 is a free edge and open to provide an area for the patient's neck to extend through during use). Accordingly, the side static walls 51 and the side movable walls 71 in a pediatric shield structure 20 are approximately the same size as the top static wall 53 and the top movable wall 73 in the pediatric shield structure 20. Comparatively, the side static walls 51 and the side movable walls 71 in an adult shield structure 20 are larger than (in particular longer than) the top static wall 53 and the top movable wall 73 in the adult shield structure 20.

It is understood that the shield structure 20 may be used with a variety of different types of procedures to visualize hard and/or soft tissue, including but not limited to percutaneous radiologic procedures and with different types of radiation 122, including but not limited to x-rays. Since the shield structure 20 blocks radiation 122 from entering into the patient's head and neck, the shield structure 20 may be used within radiologic procedures in which the patient's head and neck do not need to be examined or exposed to radiation 122. However, the shield structure 20 may also be used within radiologic procedures in which only a portion of the patient's head and neck is being examined (and is therefore exposed to radiation 122). For example, the shield structure 20 may be positioned relative to the patient's head and neck to such that the shield structure 20 blocks radiation 122 from entering into a portion of the patient's head and/or neck, while allowing another portion of the patient's head and/or neck to be exposed to radiation 122. Furthermore, since the shield structure 20 may not be secured to the table 110 (according to one embodiment), the shield structure 20 can easily be completely removed from the table 110 in the event that the practitioner would like to expose the patient's entire head and neck to radiation.

The various materials within the shield structure 20 are used to prevent corrosion since the shield structure 20 will be used around and with various cleaning detergents and saline solutions. Furthermore, the various components of the shield structure 20 are designed to be easily cleaned.

In order to support and stabilize the patient's head (and neck) during radiologic procedures and increase the comfort of the patient 10, one of the conventional non-shielding supports 220 (as shown in FIGS. 18A-21C and as described further herein) may be used in conjunction with the shield structure 20. For example, the non-shielding supports 220 may be placed on top of the inner surface 32 of the lower wall 30, within the shield structure 20, in order to provide an specific area within the shield structure 20 for the patient 10 to rest their head on. The lower wall 30 is large enough in order to fit a non-shielding support 220 on the inner surface 32 of the lower wall 30 and between the static walls 50.

The shield structure 20 may include additional components in order to hold certain medical devices during the radiologic procedure. For example, the static walls 50 may include a mechanism to attach to, hold, and support or tether a tracheal tube, such as an endotracheal tube.

Lower or Bottom Wall

As shown in FIGS. 2A-2B, the lower or bottom panel, shield, or wall 30 is configured to extend along the back of the patient's head and neck and contain a radiation attenuating material in order to block radiation 122 from entering into the patient's head and/or neck from behind the patient 10 (when the patient 10 is laying with their back against the top surface of the table 110 and facing the ceiling). However, depending on the position of the patient 10 with respect to the shield structure 20, the lower wall 30 may extend along other portions of the patient's head and neck, such as the front or sides of the patient's head and neck. The lower wall 30 extends substantially horizontally, is positioned along a lower portion of the shield structure 20, and is the base of the shield structure 20.

As shown in FIGS. 3 and 5A-5B, the lower wall 30 includes an inner (or upper) surface 32, an outer (or lower) surface 34, a top edge 36, a bottom edge 38, and two side edges 39. The inner surface 32 and the outer surface 34 are opposite each other, optionally substantially parallel to each other, and significantly larger in surface area than each of the edges 36, 38, 39. The top edge 36 and the bottom edge 38 are opposite each other and optionally substantially parallel to each other. The two side edges 39 are opposite each other and optionally substantially parallel to each other. The inner surface 32 and the outer surface 34, the top edge 36 and the bottom edge 38, and the two side edges 39 are substantially perpendicular to each other.

The outer surface 34 of the lower wall 30 is positioned along and rests on top of the top surface of the table 110 such that the table 110 is below the outer surface 34 of the lower wall 30, and the outer surface 34 faces toward the top surface of the table 110 (as shown in FIGS. 2A-2B). The lower wall 30 is optionally substantially parallel to the top surface of the table 110. The patient rests their head (directly or indirectly) on the inner surface 32 of the lower wall 30 such that the patient's head and neck are above the inner surface 32 of the lower wall 30, and the inner surface 32 faces the patient's head and neck when being used. Accordingly, the lower wall 30 is sandwiched between the patient's head and neck region and the table 110.

Each of the static walls 50 are statically attached to three of the four edges of the lower wall 30 and extend substantially perpendicularly to the lower wall 30. In particular, each of the static walls 50 are attached to and extend along the top edge 36 or one of the two side edges 39 of the lower wall 30. Each of the movable walls 70 also extend along the top edge 36 or one of the two side edges 39 of the lower wall 30. Accordingly, the static walls 50 and the movable walls 70 may each be side walls or top walls, depending on their position along the lower wall 30. Neither the static walls 50 nor the movable walls 70 extend along the entire length of the bottom edge 78 of the lower wall 30 in order to provide an area for the patient's neck to extend through while their head is on top of the lower wall 30. However, according to one embodiment, the static walls 50 and the movable walls 70 may optionally extend along a portion of the bottom edge 78 of the lower wall 30 in order to provide additional shielding while still providing an open area along the bottom edge 78 that is wide enough to accommodate the width of the patient's neck. Accordingly, the top edge 36 of the lower wall 30 extends along the top of the patient's head, each of the side edge 39 of the lower wall 30 extend along the each of sides of the patient's head (or the front or back of the patient's head, depending on the position of the patient), and the bottom edge 38 extends along the width of the neck of the patient.

As shown in FIG. 5B, the lower wall 30 preferably includes multiple layers. For example, the lower wall 30 includes at least one structural or supporting layer 42 and at least one shielding layer 44. Both the static walls 50 and the movable walls 70 (as described further herein) also preferably include the supporting layers 42 and the shielding layer 44. However, according to another embodiment, the lower wall 30, the static walls 50, and/or the movable walls 70 only include one layer (i.e., the shielding layer 44).

According to one embodiment, the shielding layer 44 is sandwiched or positioned in between two supporting layers 42. All of the walls 30, 50, 70 (and their components) may be constructed in order to be solvent resistant and resilient in order to maintain their integrity while being cleaned with hospital cleaners (i.e., provides a resilient barrier to, and that will not be denatured by, hospital disinfectants currently registered with the Environmental Protection Agency (EPA). Additionally, the walls 30, 50, 70 (and their components) may be at least partially covered in and/or bonded by an epoxy resin in order to provide a protective outer barrier for increased strength and in order to be structurally resistant to various disinfectants or cleaning solutions (such that the structural integrity of the shield structure 20 does not decrease as a result of being cleaned or disinfected).

The outer shell or supporting layer 42 is configured to provide structure or support for and at least partially cover the shielding layer 44. Accordingly, the supporting layer 42 may be constructed out of a variety of different materials that provide structure or support without being obtrusive to the patient or the practitioners, including but not limited to carbon fiber (which is strong, lightweight, and radiolucent), plastic, sealed wood, or aluminum. In a particularly preferred embodiment, resin-infused carbon fiber may be used. Additionally, the supporting layer 42 may prevent the patient and practitioners from coming in direct contact with the shielding layer 44. Further, the supporting layer 42 preferably provides a desired resilient barrier. Accordingly, the supporting layer 42 may extend around all of the edges of the shielding layer 44 (as well as the two opposite sides of the shielding layer 44), thereby fully encapsulating or surrounding the shielding layer 44.

The shielding layer 44 is configured to block or attenuate radiation 122. Accordingly, the shielding layer 44 may be constructed out of a variety of different materials that block or attenuate radiation 122, including but not limited to lead and/or aluminum. For example, the shielding layer may be a 0.02 to 0.039 inch (i.e., 0.5 to 1 millimeter) thick sheet of lead.

The supporting layer 42 and the shielding layer 44 may have a variety of different thicknesses, according to the desired configuration. According to one embodiment, the supporting layer thickness ST may be approximately 0.125 inches, and the shielding layer thickness TS may be approximately 0.039 inches such that the total thickness TT of the lower wall 30 (i.e., both of the supporting layers 42 and the shielding layer 44) is approximately 0.289 inches.

Static or Side Wall

As shown in FIGS. 2A-2B, the static or side panels, shields, or walls 50 are configured to extend along the sides and top of the patient's head and neck and contain a radiation attenuating material in order to block radiation 122 from entering into the patient's head and/or neck from either side or the top of the patient 10 (when the patient 10 is laying with their back against the top surface of the table 110, facing the ceiling). However, depending on the position of the patient 10 with respect to the shield structure 20, the static walls 50 may extend along other portions of the patient's head and neck, such as the front or back of the patient's head and neck. As described further herein, the static walls 50 may preferably include the supporting layers 42 and the shielding layer 44.

As shown in FIGS. 3 and 6A-6B, the static wall 50 includes an inner surface 52, an outer surface 54, a top edge 56, a bottom edge 58, and two side edges 59. The inner surface 52 and the outer surface 54 are opposite each other, optionally substantially parallel to each other, and significantly larger in surface area than each of the edges 56, 58, 59. The top edge 56 and the bottom edge 58 are opposite each other and optionally substantially parallel to each other. The two side edges 59 are opposite each other and optionally substantially parallel to each other. The inner surface 52 and the outer surface 54, the top edge 56 and the bottom edge 58, and the two side edges 59 are substantially perpendicular to each other.

The static walls 50 are positioned substantially vertically (i.e., are substantially perpendicular to the lower wall 30 and the top surface of the table 110). The outer surface 54 of the static wall 50 faces away from an inner region of the shield structure 20 (i.e., where the patient's head and neck are positioned) and away from the patient 10. Additionally, the outer surface 54 of the static wall 50 faces toward the movable wall 70 (in particular toward the inner surface 72 of the movable wall 70) and is configured to movably attach with the movable wall 70 (as described further herein). The inner surface 52 of the static wall 50 faces toward the patient 10 and toward the inner region of the shield structure 20. Depending on position of the patient's head within the shield structure 20 and where the static wall 50 is positioned along the lower wall 30, the inner surface 52 of the static wall 50 may face the top, sides, front, or back of the patient's head and neck when the shield structure 20 is being used.

The static walls 50 are statically attached to the lower wall 30, specifically to or along three of the four edges of the lower wall 30 (as described further herein). Depending on the position of the static wall 50 relative to the lower wall 30, the static wall 50 is either a side static wall 51 or a top static wall 53 (as shown in FIG. 3). In particular, each of the bottom edges 58 of the side static walls 51 are positioned or extend along and are statically attached to one of the two side edges 39 of the lower wall 30. The bottom edge 58 of the top static wall 53 is positioned or extends along and is statically attached to the top edge 36 of the lower wall 30. Accordingly, the side static walls 51 and the top static wall 53 are substantially perpendicular to and adjacent to each other (and the side static walls 51 are optionally substantially parallel to and spaced apart from each other). One side edge 59 of each of the side static walls 51 is positioned or extending along and statically attached to a side edge 59 of the top static wall 53 (and the other side edge 59 of the side static walls 51 is a free edge and not attached to another wall in order to provide a space for the patient's neck). Accordingly, both side edges 59 of the top static wall 53 are attached to and extend along respective side edges 59 of the two side static walls 51, thereby forming two corners along opposite side edges 59 of the top static wall 53. The top edges 56 of all of the static walls 50 are free edges and not attached to another wall in order to provide space and an open area above the shield structure 20, which may be particularly beneficial in order to provide the patient 10 with a visually open space when facing upwards and to allow the practitioner to easily access the patient 10.

According to one embodiment, the base portion of the static wall 50 (that extends along the bottom edge 58 of the static wall 50) may be thicker than the top portion of the static wall 50 (that extends along the top edge 56 of the static wall 50) in order to improve the connection between the static wall 50 and the lower wall 30, thereby improving the support of the static wall 50 and the overall stability of the shield structure 20. For example, the static wall 50 may be tapered along its height such that the static wall 50 does not intersect with the lower wall 30 at exactly 90°.

Optionally, the static wall 50 may be a part of a wall set 90 (as described further herein and as shown in FIGS. 3 and 9C) that includes both the static wall 50 and a corresponding movable wall 70. Accordingly, the static wall 50 and the movable wall 70 are movably attached and detachable (and reattachable) to each other. In order to include such a configuration, the static wall 50 includes a static connection portion 60 that includes at least one static guide 62 and at least one receiver 66 attached to the outer surface 54 of the static wall 50, as shown in FIGS. 6A-6B.

The static guide 62 is configured to interlock with the movable guide 82 of the movable connection portion 80 (as described further herein). As shown in FIG. 6A, the static connection portion 60 includes at least one set of static guides 62. According to one embodiment, the static connection portion 60 includes at least two sets of static guides 62 that are horizontally spaced apart from each other along the width of the static wall 50. Each of the sets of static guides 62 includes multiple static guides 62. According to one embodiment, each of the sets of static guides 62 includes three static guides 62, although it is understood that each of the sets of static guides 62 can include any number of static guides 62. Within a set of static guides 62, the static guides 62 are vertically aligned with each other (and vertically spaced apart from each other) in a row extending along the height of the static wall 50.

As shown in FIG. 6B, each of the static guides 62 includes an extension 63 and a catch portion 64 (e.g., a hook or latch). The extension 63 extends substantially perpendicularly out from the outer surface 54 of the static wall 50, thereby spacing the catch portion 64 out from the outer surface 54 of the static wall 50. The catch portion 64 optionally extends substantially perpendicularly to the extension 63 (and therefore substantially parallel to the outer surface 54 of the static wall 50). As shown in FIG. 6A (in view of FIG. 6B), the catch portion 64 may be substantially cylindrical with substantially circular outer and inner surfaces. As shown in FIG. 6B, the extension 63 may be attached to a middle portion of the catch portion 64 such that the catch portion 64 extends beyond both sides of the extension 63 (since the extension 63 has a smaller width than the catch portion 64). Accordingly, the static guides 62 may have a "T-bolt" configuration.

The receivers 66 are configured to interlock with the fastener 86 of the movable connection portion 80 (as described further herein). As shown in FIG. 6A, multiple receivers 66 are positioned along the height of the static wall 50 and aligned vertically with each other (and spaced apart from each other vertically), thereby defining different discrete positions that the movable wall 70 (in particular the fastener 86) can be locked into. The movable connection portion 80 may include any number of receivers 66, according to the desired configuration (e.g., according to the desired number and location of positions that the movable wall 70 can be locked into). According to one embodiment, the movable connection portion 80 includes three or four receivers 66. The receivers 66 may be apertures, recesses, or holes that do not extend completely through the static wall 50 (in order to avoid any interference with the shielding provided by the static wall 50). The receivers 66 may be positioned along and within a reinforced receiver support 68 that is attached to the outer surface 54 of the static wall 50 (with, for example, an adhesive such as epoxy) such that the receivers 66 do not protrude at all into the outer surface 54 of the static wall 50. The receiver support 68 may be constructed out of a variety of different supportive materials, including but not limited to carbon fiber. According to another embodiment, the receiver 66 may be a slot that extends along the height of the static wall 50 and is configured to receive and be secured to the fastener 86.

The static wall 50 may have a variety of different dimensions, according to the desired configuration. For example, according to one embodiment as shown in FIG. 6A, the distance D1 between the center of one of the static guides 62 and the nearest side edge 59 of the static wall 50 may be approximately 3.125 to 5 inches (for example, 4 inches), and the distance D2 between the center of one of the top-most positioned static guides 62 and the top edge 56 of the static wall 50 may be approximately 0.5 inches. The distance D3 between the centers of two adjacent static guides 62 within one set of static guides 62 may be approximately 1.75 inches. The distance D4 between the center of the row of receivers 66 and a side edge 59 of the static wall 50 may be approximately 5 to 7.5 inches (for example, 6 inches). The distance D5 between the edge of the receiver support 68 and the nearest side edge 59 of the static wall 50 may be approximately 4.5 to 7 inches (for example, 5.5 inches).

Furthermore, as shown in FIG. 9A, the distance D6 between the side edge 59 and the closest edge of the receiver support 68 may be approximately 4.5 to 7 inches (for example, 5 inches), and the distance D7 between the side edge 59 and the furthest edge of the receiver support 68 may be approximately 5.5 to 8 inches (for example, 7 inches). The depth D8 of the receiver support 68 may be approximately 0.3 inches, and the depth D9 of the static guide 62 may also be approximately 0.3 inches. The width D10 of the extension 63 may be approximately 0.1 inches, and the width D11 of the catch portion 64 may be approximately 0.5 inches. The depth D12 of the extension 63 may be approximately 0.2 inches. The thickness or depth D13 of the static wall 50 may be approximately 0.25 inches.

Movable Wall

As shown in FIGS. 2A-2B, the movable panels, shields, or walls 70 are configured to extend along the sides and top of the patient's head and neck in order to further block radiation 122 from entering into the patient's head and/or neck from either side or the top of the patient 10 (when the patient 10 is laying with their back against the top surface of the table 110 and facing the ceiling), in addition to the static walls 50. However, depending on the position of the patient 10 with respect to the shield structure 20, the movable walls 70 may extend along other portions of the patient's head and neck, such as the front or back of the patient's head and neck. As described further herein, the movable walls 70 are movable between a retracted position 96 and an extended position 98 relative to the static walls 50 and the lower wall 30 in order to optionally provide additional vertical shielding for the patient's head and neck that is at least partially vertically above the static walls 50. By allowing the movable wall 70 to move, the amount and location of shielding can be customized to the particular radiologic procedure and according to the position of the radiation source 120. As described further herein, the movable walls 70 may preferably include the supporting layers 42 and the shielding layer 44.

As shown in FIGS. 3 and 7A-7B, the movable wall 70 includes an inner surface 72, an outer surface 74, a top edge 76, a bottom edge 78, and two side edges 79. The inner surface 72 and the outer surface 74 are opposite each other, optionally substantially parallel to each other, and significantly larger in surface area than each of the edges 76, 78, 79. The top edge 76 and the bottom edge 78 are opposite each other and optionally substantially parallel to each other. The two side edges 79 are opposite each other and optionally substantially parallel to each other. The inner surface 72 and the outer surface 74, the top edge 76 and the bottom edge 78, and the two side edges 79 are substantially perpendicular to each other.

The movable walls 70 are positioned substantially vertically (i.e., are optionally substantially perpendicular to the lower wall 30 and the top surface of the table 110 and optionally substantially parallel to the static walls 50). The outer surface 74 of the movable wall 70 faces away from an inner region of the shield structure 20 (i.e., where the patient's head and neck are positioned) and away from the patient 10. The inner surface 72 of the movable wall 70 faces toward the patient 10 and toward the inner region of the shield structure 20. Depending on position of the patient's head within the shield structure 20 and where the movable wall 70 is positioned relative to the lower wall 30, the inner surface 72 of the movable wall 70 may face the top, sides, front, or back of the patient's head and neck when being used. Additionally, the inner surface 72 of the movable wall 70 faces toward the static wall 50 (in particular toward the outer surface 54 of the static wall 50) and is configured to movably attach with the static wall 50 (as described further herein).

Each of the movable walls 70 correspond to and are movably attached to one of the static walls 50, which are statically attached to the lower wall 30 (as described further herein). Depending on the position of the movable wall 70 relative to the lower wall 30, the movable wall 70 is either a side movable wall 71 or a top movable wall 73 (as shown in FIG. 3). In particular, each of the side movable walls 71 are positioned or extend along one of the two side edges 39 of the lower wall 30 and one of the two side static walls 51. The top movable wall 73 is positioned or extends along the top edge 36 of the lower wall 30 and the top static wall 53. Accordingly, the side movable walls 71 and the top movable wall 73 are optionally substantially perpendicular to and adjacent to each other (and the side movable walls 71 are optionally substantially parallel to and spaced apart from each other).

In order to be independently movable relative to each other, the movable walls 70 are only attached to the rest of the shield structure 20 through a connection mechanism 94 (as described further herein) that movably attaches each of the inner surfaces 72 of the movable walls 70 to a respective one of the static walls 50. Accordingly, the side edges 79 of each of the movable walls 70 are not attached to each other. Even further, the top edges 76, the bottom edges 78, and the side edges 79 of all of the movable walls 70 are free edges and are not attached to another wall or portion of the shield structure 20. By having the top edges 76 of the movable walls 70 as free edges, the shield structure 20 provides space and an open area above the shield structure 20, which may be particularly beneficial in order to provide the patient 10 with a visually open space when facing upwards and to allow the practitioner to easily access the patient 10.

The movable wall 70 is a part of the wall set 90 (as described further herein and as shown in FIGS. 3 and 9C) that includes both the movable wall 70 and a corresponding static wall 50. Accordingly, the static wall 50 and the movable wall 70 are movably attached and detachable (and reattachable) to each other. In order to include such a configuration, the movable wall 70 includes a movable connection portion 80 that includes at least one movable guide 82 and at least one fastener 86 attached to the inner surface 72 of the movable wall 70, as shown in FIGS. 7A-7B.

The movable guide 82 is configured to interlock with the static guide 62 of the static connection portion 60 (as described further herein) and is statically attached to and movable with the movable wall 70. The movable connection portion 80 may include any number of movable guides 82. As shown in FIG. 7A, the movable connection portion 80 includes two movable guides 82 that are horizontally spaced apart from each other along the width of the movable wall 70. The movable guides 82 are vertically oriented such that the movable guides 82 extend along at least a portion of the height of the movable wall 70. According to one embodiment, the movable guides 82 extend along the entire height of the movable wall 70 (i.e., from the bottom edge 78 to top edge 76) in order to allow the movable wall 70 to be securely moved along the entire distance between the retracted position 96 and the extended position 98.

As shown in FIG. 7B, each of the movable guides 82 includes at least one extension 83 and at least one catch portion 84 (e.g., a hook or latch). The extension 83 extends substantially perpendicularly out from the inner surface 72 of the movable wall 70, thereby spacing the catch portion 84 out from the inner surface 72 of the movable wall 70. The catch portion 84 optionally extends substantially perpendicularly to the extension 83 (and therefore optionally substantially parallel to the inner surface 72 of the movable wall 70). As shown in FIG. 7A, the catch portion 84 may extend along the height of the movable wall 70. As shown in FIG. 7B, the extension 83 may be attached to an end of the catch portion 84 such that the catch portion 84 extends to one side of the extension 83.

As shown in FIG. 7B, each of the movable guides 82 may include two extensions 83 that are spaced apart from each other along the width of the movable wall 70. Each of the extensions 83 may have a corresponding catch portion 84 that extends toward each other catch portion 84 of that movable guide 82, thereby forming a track, slot, clamp, or rail that extends lengthwise along the height of the movable wall 70. The movable guide 82 may optionally further include a base 81 that extends along the length of the movable guide 82, extends optionally parallel to the inner surface 72 of the movable wall 70, and is positioned in between both of the extensions 83 and the inner surface 72 of the movable wall 70, thereby connecting the extensions 83 to the inner surface 72.

The fastener 86 is configured to interlock with the receiver 66 of the static wall 50 (as described further herein). As shown in FIG. 7A, the fastener 86 is positioned close to or along the bottom edge 78 of the movable wall 70, which maximizes how much the movable wall 70 can be adjusted relative to and above the static wall 50. The fastener 86 extends completely through the movable wall 70 in order to provide a handle on the outer surface 74 of the movable wall 70 for the practitioner to grasp (in order to adjust the position of the movable wall 70) and in order to extend into the receiver 66 on the static wall 50 (in order to lock the movable wall 70 into a particular position).

The fastener 86 may be, for example, a bolt, a pin, a ring pull bolt, spring bolt, or a spring bolt lock. According to one embodiment, the fastener 86 may be a conventional spring plunger, as shown in FIGS. 8A-8D. The spring plunger includes a shaft 87, a movable pin 88 (e.g., a plunger or detent), and a spring 89. The spring plunger may optionally include threads, as shown in FIG. 8A. As shown in FIGS. 8B-8C, the pin 88 is movable within the shaft 87. The spring 89, however, is positioned at least partially within the shaft 87 and biases the pin 88 to move toward one side of the fastener 86 (i.e., away from the head of the shaft 87), as shown in FIG. 8B. The pin 88 may be retracted into the shaft 87 by moving the pin 88 against the biasing force of the spring 89 relative to the shaft 87 (as shown in FIG. 8C).

Accordingly, as shown in FIG. 7B, the fastener 86 (that is the spring plunger) is positioned such that at least the head of the pin 88 is positioned along the outer surface 74 of the movable wall 70, with the shaft 87 extending at least partially through the movable wall 70. Accordingly, the pin 88 is biased to move further into and through the movable wall 70, in a direction away from the outer surface 74 of the movable wall 70, thereby protruding out from the inner surface 72 of the movable wall 70. As described further herein, when the pin 88 is aligned with one of the receivers 66 and released, the spring 89 automatically moves the pin 88 toward and into the receiver 66, thereby locking the movable wall 70 into place.

The movable wall 70 may have a variety of different dimensions, according to the desired configuration. For example, according to one embodiment as shown in FIG. 9B, the distance D14 between the side edge 79 and the closest edge of the closest movable guide 82 may be approximately 2.75 to 4.62 inches (for example, 3.5 inches), and the distance D15 between the side edge 79 and the furthest edge of the closest movable guide 82 may be approximately 3.5 to 5.37 inches (for example, 4.25 inches). The distance D16 between the side edge 79 and the closest edge of the fastener 86 may be approximately 4.5 to 7 inches (for example, 5 inches), and the distance D17 between the side edge 79 and the furthest edge of the fastener 86 may be approximately 5.5 to 8 inches (for example, 7 inches).

Additionally, the depth D18 of the movable guide 82 may be approximately 0.3 inches, the distance D19 between the closest ends of the two catch portions 84 may be approximately 0.2 inches, and the distance D20 between the catch portion 84 and the base 81 may be approximately 0.2 inches. The thickness or depth D21 of the movable wall 70 may be approximately 0.125 inches.

According to another embodiment, the movable guide 82 may alternatively have the configuration of the static guide 62, and vice versa.

Wall Set

As shown in FIGS. 3 and 9C, the shield structure 20 may include at least one wall set 90 that includes a static wall 50 and a corresponding movable wall 70 that are optionally substantially parallel to each other and movably attached to each other. The shield structure 20 may include multiple wall sets 90 (for example, three wall sets 90) that are attached to the lower wall 30. Each of the wall sets 90 includes a connection mechanism 94 (as described further herein) that movably attaches the movable wall 70 to the static wall 50.

Depending on the position of the wall set 90 relative to the lower wall 30, the wall set 90 is either a side wall set 91 or a top wall set 93 (as shown in FIG. 3). In particular, the side wall set 91 includes a side static wall 51 and a side movable wall 71, each of which are described further herein. The top wall set 93 includes a top static wall 53 and a top movable wall 73, each of which are also described further herein.

Although three wall sets 90 are shown, the shield structure 20 may include any number of wall sets 90 (or any number of independent static walls 50) (i.e., more or less than three wall sets 90 or than three static walls 50) depending on the desired configuration, depending on the shape and size of the lower wall 30, and in order to optimize the shielding and surround the patient's head and neck while providing the practitioner access to the patient's head and neck. Each of the wall sets 90 may be different or the same sizes.

Furthermore, each of the wall sets 90 may have different shapes, depending on the desired configuration. For example, the static wall 50 and the movable wall 70 may each be substantially flat. According to another embodiment, the static wall 50 and/or the movable wall 70 may be at least partially curved.

However, according to another embodiment, the shield structure 20 may have only independent static walls 50 (i.e., without any corresponding movable walls 70) or may include some static walls 50 without a corresponding movable wall 70 and some static walls 50 with a corresponding movable wall 70.

Connection Mechanism

As shown in FIGS. 6A-9C, the shield structure 20 includes at least one connection mechanism 94 that movably and adjustably attaches the movable wall 70 to the static wall 50 in order to allow the movable wall 70 to move and be adjusted between the retracted position 96 and the extended position 98. Furthermore, the connection mechanism 94 allows the movable wall 70 to be completely removed from (and reattached to) the static wall 50 in order to easily clean or sanitize the various parts of the shield structure 20.

In particular, the connection mechanism 94 movably attaches the inner surface 72 of the movable wall 70 to the outer surface 54 of the static wall 50. Accordingly, the connection mechanism 94 includes the movable connection portion 80 (as described further herein) that is located on and included as a part of the movable wall 70 and the static connection portion 60 (as described further herein) that is located on and included as a part of the static wall 50. The movable connection portion 80 and the static connection portion 60 are complementary to and correspond with each other.

The size of the various components of the movable connection portion 80 and the static connection portion 60 are complementary to each other in order to allow the various components of the movable connection portion 80 and the static connection portion 60 to interlock and fit with each other. Additionally, the respective positions of the various components of the movable connection portion 80 and the static connection portion 60 correspond and align with each other in order to allow the various components of the movable connection portion 80 and the static connection portion 60 to attach each other. The number of sets of static guides 62 and the number of movable guides 82 also correspond to each other.

As shown in FIG. 9C, the movable guides 82 and the static guides 62 interlock with each other in order to guide the vertical movement of the movable wall 70 between the retracted position 96 and the extended position 98. Additionally, by interlocking with each other, the movable guides 82 and the static guides 62 horizontally secure the movable wall 70 relative to the static wall 50 once the movable wall 70 is locked into a certain position. In order to interlock with each other, the catch portions 64 of the static guides 62 are moved or slide into an opening within the movable guide 82 (through the top or bottom of the movable guide 82). This opening within the movable guide 82 extends along the length of the movable guide 82 (and along the length of the movable wall 70) and is formed between the pairs of extensions 83 and between the catch portions 84 and the base 81. When attached to each other, the extensions 63 of the static guides 62 extend through the gap between the two catch portions 84 of the movable guide 82. The catch portions 64 and 84 prevent the movable guides 82 and the static guides 62 from horizontally detaching from each other.

As further shown in FIG. 9C, the receiver 66 and the fastener 86 interlock with each other in order to lock the movable wall 70 into position (relative to the static wall 50) and to vertically secure the movable wall 70 relative to the static wall 50. In order to interlock with each other, the practitioner releases the fastener 86, which automatically moves the pin 88 away from the inner surface 72 of the movable wall 70 (and thereby toward the outer surface 54 of the static wall 50, in particular toward the outer surface of the receiver support 68). Once the pin 88 is aligned with one of the receivers 66, the pin 88 can move further away from the inner surface 72 of the movable wall 70 by moving into the receiver 66, thereby securing the fastener 86 and the receiver 66 together.

Shield Structure Use and Adjustment

In order to use the shield structure 20, the shield structure 20 may simply be placed on the top surface of the table 110, and the patient 10 may position their head in the inner area of the shield structure 20. Without any modifications or mechanical attachments to the table 110 or any further adjustments, the shield structure 20 provides radiation shielding to the patient's head and neck. Accordingly, the shield structure 20 is easily usable within radiologic procedures and can be used by the practitioner with a minimal understanding of radiation protection in order to provide maximum head and neck radiation protection of the patient.

The shield structure may be used with static walls or walls maintained in a static position, as shown in certain disclosed embodiments. Additionally, as shown in FIGS. 10A-11B, the shield structure 20 may be easily vertically adjusted in order to provide additional shielding, if desired. Accordingly, at least one of the movable walls 70 may be moved vertically between the retracted position 96 and the extended position 98 relative to the static wall 50 before, during, and/or after the radiologic procedure in order to customize the amount and location of shielding from radiation 122 to the patient's head and neck and to provide more or less access to the patient's head and neck for the practitioner. The amount and positioning of shielding of the patient's head and neck may depend on the views for examination that are needed, the angle of the radiation 122, where and how the practitioner needs to access the patient 10, and the position of the radiation source 120.

Each of the movable walls 70 can be movable between and secured into the retracted position 96 (as shown in FIGS. 10A and 11A), into a variety of different partially retracted (or partially extended) positions that are between the retracted position 96 and the extended position 98, or into the extended position 98 (as shown in FIGS. 10B and 11B), depending on the desired amount of shielding and amount of access to the patient's head and neck for the practitioner. The location and number of partially retracted (or partially extended) positions that the movable wall 70 can be secured into depends on the number of receivers 66. In the retracted position 96, the shield structure 20 provides the maximum amount of access to the patient's head and neck for the practitioner. In the extended position 98, the shield structure 20 provides the maximum amount of radiation shielding to the patient's head and neck.

In order to move the movable wall 70, the practitioner first grasps a portion of the fastener 86 (such as the head of the pin 88) and pulls the pin 88 in a direction out of the movable wall 70 and away from the movable wall 70 and the static wall 50, thereby overcoming the biasing force of the spring 89, moving the pin 88 out of the receiver 66, and unlocking the movable wall 70 from the static wall 50. The practitioner can then move or slide the movable wall 70 up or down (depending on the original position of the movable wall 70) into the desired position. Once the desired position is reached, the practitioner releases the pin 88, which allows the spring 89 to automatically move the pin 88 further back into the movable wall 70 and toward the static wall 50. Once the pin 88 is aligned with one of the receivers 66, the spring 89 automatically moves the pin 88 further toward the static wall 50 and into the receiver 66 (i.e., back to its original position relative to the movable wall 70), thereby locking the movable wall 70 to the static wall 50.

Since the movable walls 70 are only attached to the rest of the shield structure 20 through the connection mechanism 94, all of the movable walls 70 are independently adjustable and movable between the retracted position 96 and the extended position 98. This configuration allows the practitioner to more easily access certain areas of the patient's head and neck during the radiologic procedure while still minimizing the radiation exposure to the patient's head and neck. Accordingly, some of the movable walls 70 may be positioned in the retracted position 96 while other movable walls 70 may be positioned in the extended position 98, as shown in FIGS. 10A-10B and 12A-12C. For example, as shown in FIG. 10A, all of the movable walls 70 are in the retracted position 96. As shown in FIG. 12A, only the top movable wall 73 is in the extended position 98, and both of the side movable walls 71 are in the retracted position 96. As shown in FIG. 12B, only one of the side movable walls 71 is in the extended position 98, and the top movable wall 73 and the other side movable wall 71 are both in the retracted position 96. As shown in FIG. 12C, the top movable wall 73 and one of the side movable walls 71 are both in the extended position 98, and the other side movable wall 71 is in the retracted position 96. As shown in FIG. 10B, all of the movable walls 70 are in the extended position 98. Additionally, the shield structure 20 may be adjusted such that both of the side movable walls 71 are in the extended position 98, and the top movable wall 73 is in the retracted position 96.

FIG. 13 shows how the shield structure 20 is open above the static walls 50 and movable walls 70, which allows the practitioner to easily access the patient 10 from above the shield structure 20 while the patient 10 is protected from the sides, top, and bottom of their head and neck from radiation 122 due to the shield structure 20. FIG. 14 shows how the shield structure 20 protects the top of the patient's head.

Shield Structure with Skirt Assembly

Figure 22:
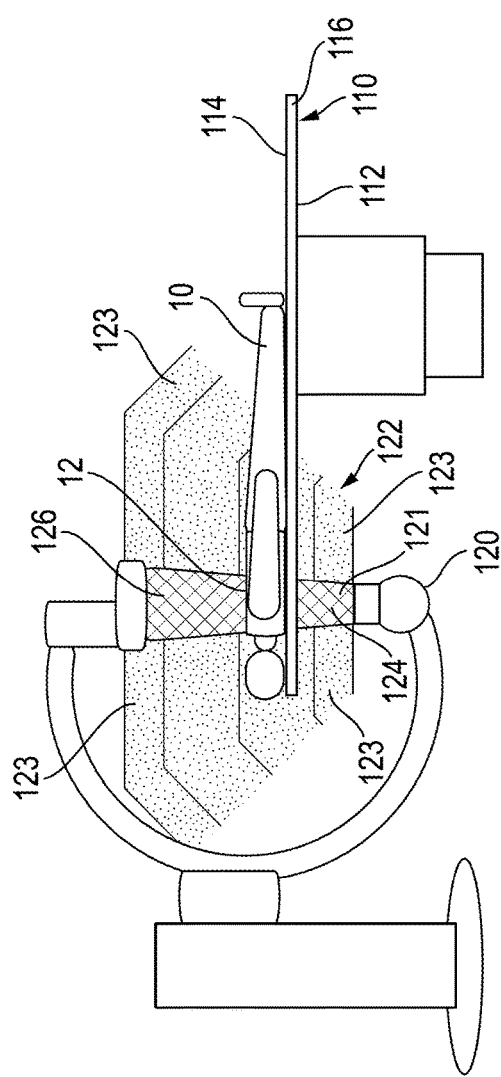
FIG. 22 is a side view of a patient, while being exposed to radiation from a radiation source, on a conventional examination table.

FIG. 22 shows a patient 10 on an examination table 110 without the shield structure 20 and demonstrates how areas of the patient 10 outside of the examination area 12, in particular the patient's head and neck, are exposed to radiation during imaging without the shield structure 20. According to one embodiment as shown in FIGS. 23-26, the shield structure 20 includes a skirt assembly 130 that is configured to provide additional shielding from radiation from an area along the sides of and below the table 110. In particular, the skirt assembly 130 is configured to extend below the base 22 of the radiation assembly 20, along the sides of and below the table 110.

Figure 23:
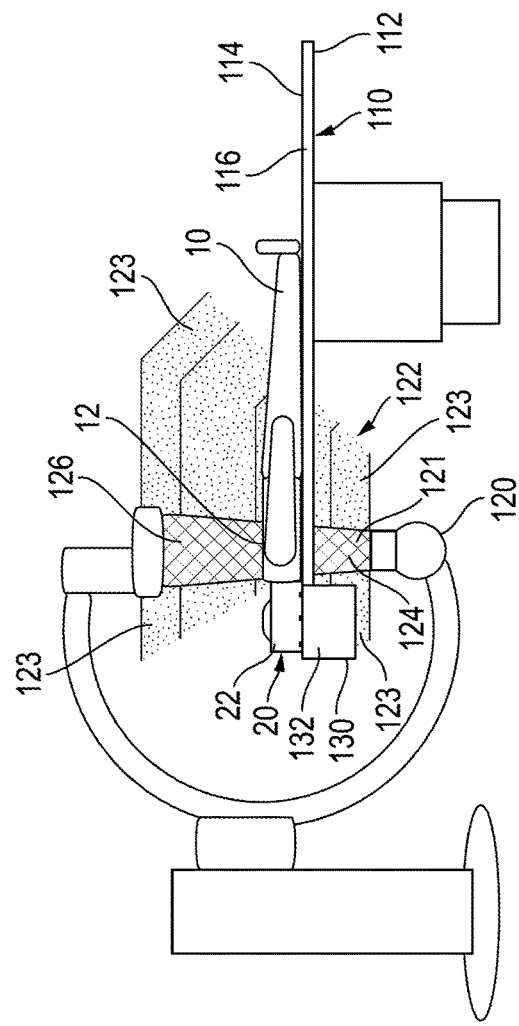
FIG. 23 is a side view of a patient, while being exposed to radiation from a radiation source, on an examination table with a shield structure according to one embodiment.
Figure 24:
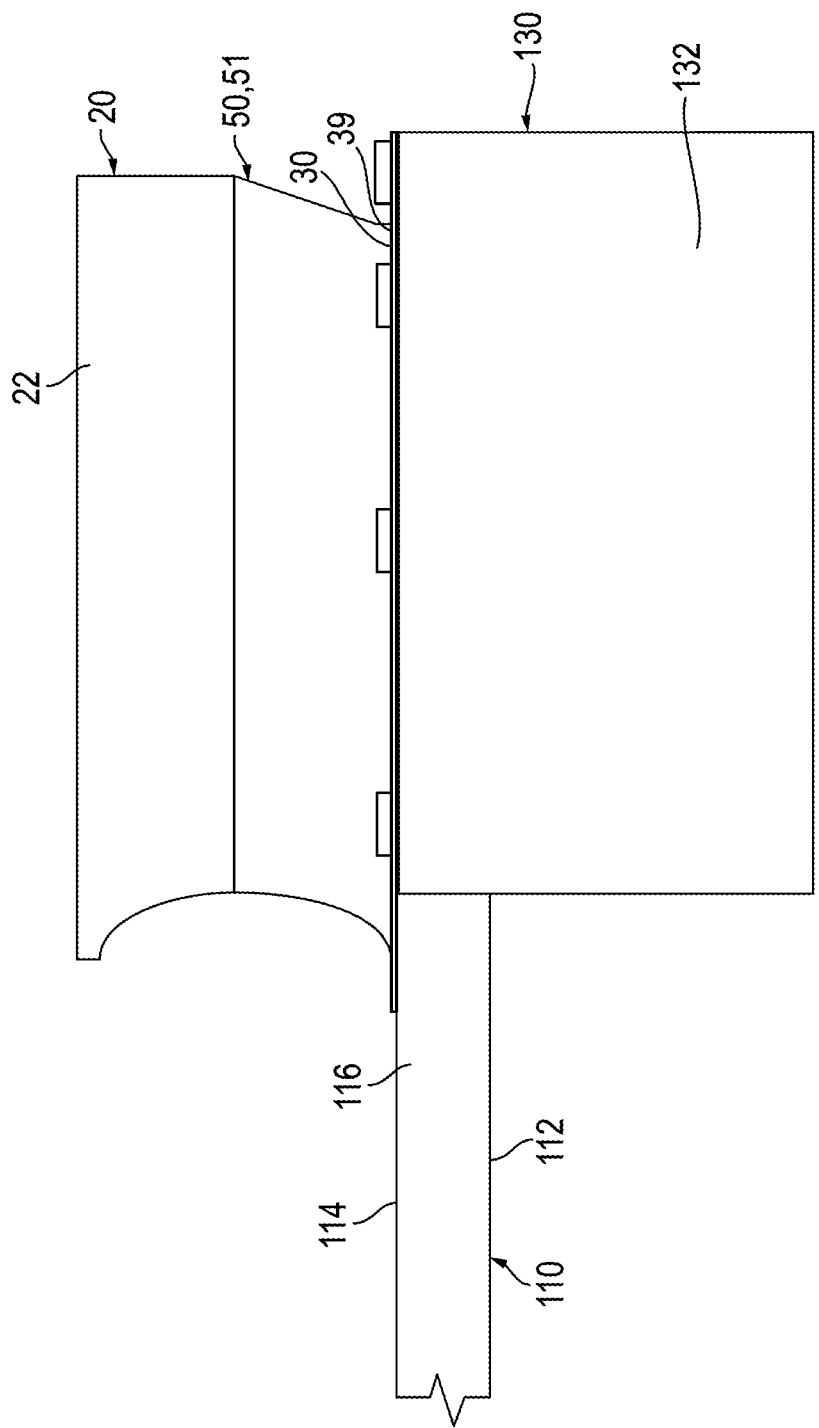
FIG. 24 is a side view of a shield structure on a table according to one embodiment that includes skirts.

In particular, the table 110 has a bottom surface 112 and a top surface 114 that are directly opposite each other. As shown in FIG. 23, the patient 10 lays on top of the top surface 114, and the base 22 of the shield assembly 20 is positioned above the table 110, along the top surface 114 of the table 110. The radiation source 120 is positioned below the table 110, along the bottom surface 112 of the table 110. The base 22, which is the portion of the shield assembly 20 that the patient's head and neck are positioned within and surrounded by and includes lower wall 30 and static walls 50 (movable walls 70 are not used in this embodiment, but could be), is positioned on top of the table 110, along the top surface 114 of the table 110. The skirt assembly 130 is attached to the base 22 of the shield assembly 20 (such as to the lower wall 30 and/or the static walls 50) by a conventional connection mechanism and extends along at least a portion of the side surfaces 116 of the table 110 (where the side surfaces 116 extend between the top surface 114 and the bottom surface 112) and below the bottom surface 112 of the table 110.

The skirt assembly 130 comprises at least one shield or skirt 132 that extends below and hangs downward relative to the base 22 of the shield assembly 20. For example, the skirt assembly 130 may include multiple skirts 132 (e.g., a first skirt, a second skirt, third skirt, etc.) that are disposed on, positioned along, and extend from different sides of the base 22, or the skirt assembly 130 may include a single skirt that is disposed on, positioned along, and extends from such different sides of the base 22. The skirt assembly 130 (e.g., each of the skirts 132) extends along at least a portion of one of the side surfaces 116 of the table 110 and below the bottom surface 112 of the table 110. The skirts 132 may be statically attached to a variety of different portions of the base 22, such as to the lower wall 30 and/or to the static walls 50.

According to one embodiment, a first skirt 132 is disposed on a first side (e.g., left side) of the lower wall 30, a second skirt is disposed on a second side (e.g., right side) of the lower wall 30 (where the first and second sides are opposite each other), and a third skirt 132 is disposed on a third side (e.g., above the patient's head, so as to extend from the first skirt to the second skirt). The first and second skirts 132 hang downward relative to the lower wall 30 such that the first and second skirts 132 extend below the bottom surface 112 of the table 110 on opposite sides of the table 110. Since the first and second skirts 132 are positioned on opposite sides of the table 110, medical personnel (such as a practitioner) may extend or dispose a body part (such as their legs) near or between the first, second, and/or third skirts 132 during use, which provides additional radiation protection to the medical personnel.

The skirt assembly 130 (e.g., each of the skirts 132) is constructed out of and includes at least a radiation-attenuating material (such as lead) in order to block radiation. Additional structural layers or materials may be alternatively provided for the skirt assembly.

Figure 25:
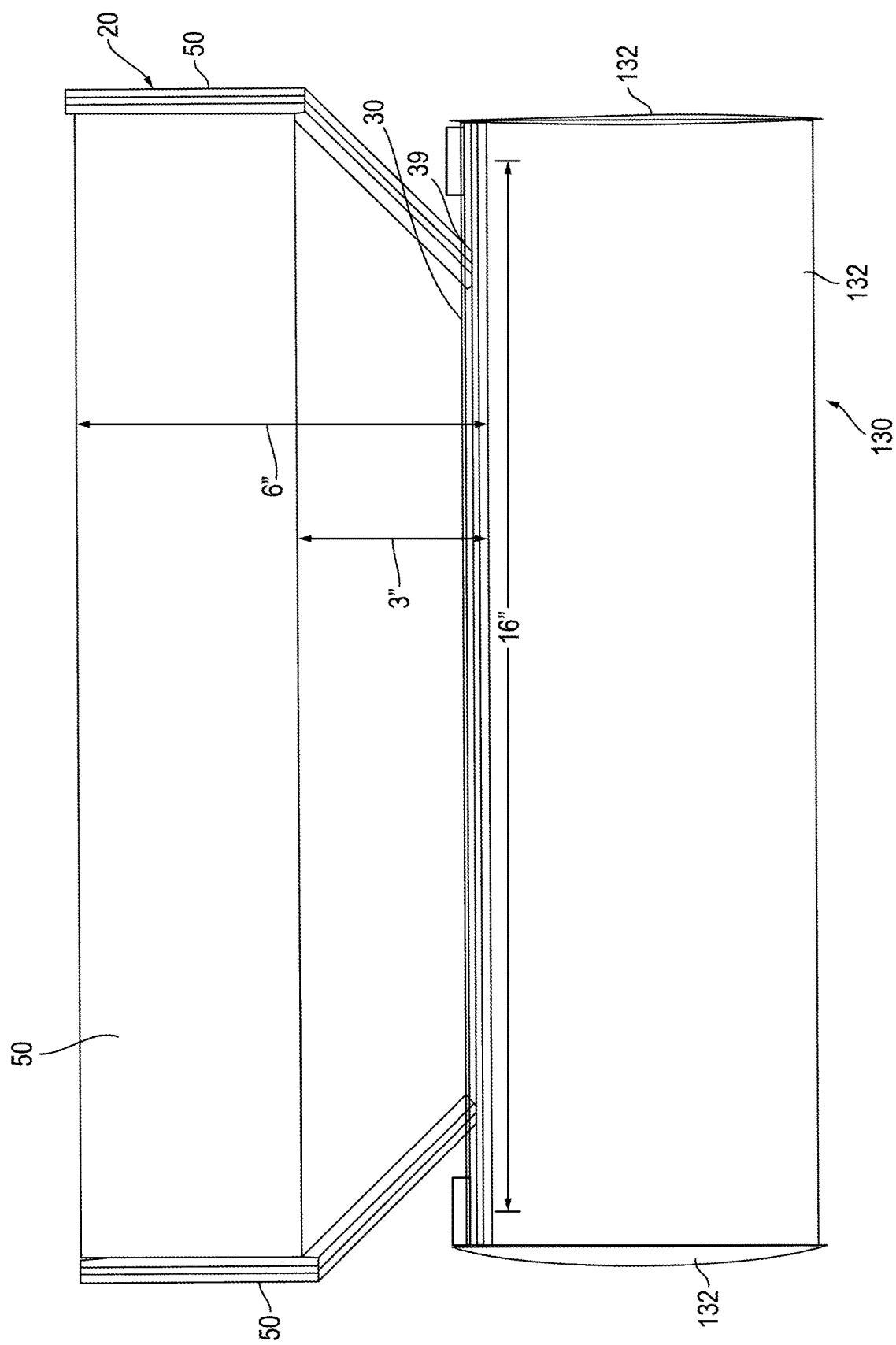
FIG. 25 is a front side view of the shield structure of FIG. 24.

According to this embodiment, the shield structure 20 can include a plurality of walls (e.g., a lower or bottom wall 30 and at least one side wall 50), that can be made of the same materials and generally configured as described in connection with the prior embodiments. However, in this embodiment, the side walls have different shape, and dimensions (in inches) of a preferred embodiment for an adult-sized shield structure are shown in FIGS. 25 and 26 (a pediatric shield structure may have smaller dimensions). While this shield structure can be used without a skirt assembly 130, it is preferred that a skirt assembly is used.

It is understood that the various relative positions, dimensions, and sizes of the various components of the shield structure 20 are exemplary only and may be changed according to the desired configuration.

The embodiments disclosed herein provide a head and neck radiation shield structure. Besides those embodiments depicted in the figures and described in the above description, other embodiments of the present invention are also contemplated. For example, any single feature of one embodiment of the present invention may be used in any other embodiment of the present invention.

Given the disclosure of the present invention, one versed in the art would appreciate that there may be other embodiments and modifications within the scope and spirit of the invention. Accordingly, all modifications attainable by one versed in the art from the present invention within the scope and spirit of the present invention are to be included as further embodiments of the present invention.

What is claimed is:

1. A shield structure configured to protect a head and/or neck of a patient during a radiologic procedure, comprising:
   a bottom shield that includes radiation attenuating material and that is configured to be positioned between the head and/or neck of the patient and a radiation source so as to shield the patient from radiation directed toward the bottom of the patient, wherein the bottom shield is of a general size to shield the head and/or neck of the patient;
   a side shield that includes radiation attenuating material and that is configured to extend upward relative to the bottom shield so as to shield the patient from radiation directed toward a side of the patient, the side shield comprising a front portion configured to be disposed proximal to the top of the head of the patient, a first side portion configured to be disposed proximal to a first side of the head of the patient, and a second side portion configured to be disposed proximal to a second side of the head of the patient;
   a first opening configured to receive the head and/or neck of the patient; and
   a second opening disposed in opposing relationship to the bottom shield and configured to allow access to the patient by extending from the front portion to the first opening.

2. The shield structure of claim 1, wherein the bottom shield and the side shield are a continuous, unitary wall structure.

3. The shield structure of claim 1, wherein the bottom shield and the side shield are separate structures.

4. The shield structure of claim 1, wherein the front portion, the first side portion, and the second side portion are a continuous, unitary structure.

5. The shield structure of claim 1, wherein the front portion, the first side portion, and the second side portion are separate structures.

6. The shield structure of claim 1, wherein the side shield includes a movable portion that is movable substantially vertically relative to the bottom shield between a retracted position and an extended position, wherein the side shield provides greater shielding to the patient when the movable portion is in the extended position.

7. The shield structure of claim 1, wherein at least one of the bottom shield and the side shield include a shielding layer that includes the radiation attenuating material, and a first structural layer that supports and at least partially covers the shielding layer.

8. The shield structure of claim 7, wherein at least one of the bottom shield and the side shield further includes a second structural layer that supports and at least partially covers the shielding layer.

9. The shield structure of claim 7, wherein the radiation attenuating material includes lead.

10. The shield structure of claim 7, wherein the first structural layer is formed of a material that provides a resilient barrier to, and that will not be denatured by, EPA-registered hospital disinfectants.

11. The shield structure of claim 10, wherein the first structural layer includes carbon fiber.

12. The shield structure of claim 1, further comprising a first skirt disposed on a first side of the bottom shield and that hangs downward relative to the bottom shield, and a second skirt disposed on a second side of the bottom shield and that hangs downward relative to the bottom shield, wherein each of the first and second skirts includes radiation attenuating material.

13. A method of protecting a head and/or neck of a patient during a radiologic procedure, comprising:
   positioning the head and/or neck of the patient in a shield structure, wherein the shield structure has a bottom shield that includes radiation attenuating material and is positioned between the head and/or neck of the patient and a radiation source, and a side shield that includes radiation attenuating material and extends upward relative to the bottom shield, wherein the side shield comprises a front portion that is disposed proximal to the top of the head of the patient, a first side portion that is disposed proximal to a first side of the head of the patient, and a second side portion that is disposed proximal to a second side of the head of the patient, wherein the head and/or neck of the patient is received in a first opening in the shield structure, and access to the patient is allowed by a second opening disposed in opposing relationship to the bottom shield and configured to extend from the front portion to the first opening; and
   exposing the patient to radiation to conduct the radiologic procedure.

14. The method of claim 13, further comprising extending a movable portion of the side shield from a retracted position to an extended position to provide greater shielding to the patient during the radiologic procedure.

15. The method of claim 13, further comprising disposing a body part of medical personnel between a first skirt disposed on a first side of the bottom shield and that hangs downward relative to the bottom shield, and a second skirt disposed on a second side of the bottom shield and that hangs downward relative to the bottom shield, wherein each of the first and second skirts includes radiation attenuating material.

16. A shield structure configured to protect a head and/or neck of a patient during a radiologic procedure, comprising:
   a bottom shield that includes radiation attenuating material and that is configured to be positioned between the head and/or neck of the patient and a radiation source so as to shield the patient from radiation directed toward the bottom of the patient, wherein the bottom shield is of a general size to shield the head and/or neck of the patient;
   a side shield that includes radiation attenuating material and that is configured to extend upward relative to the bottom shield so as to shield the patient from radiation directed toward a side of the patient; and
   an opening configured to receive the head and neck of the patient,
   wherein the side shield has a length such that an area immediately below the neck of the patient remains exposed from the shield structure.

17. The shield structure of claim 16, wherein the bottom shield and the side shield are a continuous, unitary wall structure.

18. The shield structure of claim 16, wherein the bottom shield and the side shield are separate structures.

19. The shield structure of claim 16, further comprising a first skirt disposed on a first side of the bottom shield and that hangs downward relative to the bottom shield, and a second skirt disposed on a second side of the bottom shield and that hangs downward relative to the bottom shield, wherein each of the first and second skirts includes radiation attenuating material.

\* \* \* \* \*